US007245958B1

(12) United States Patent
Navab et al.

(10) Patent No.: US 7,245,958 B1
(45) Date of Patent: Jul. 17, 2007

(54) TRIGONOMETRIC DEPTH GAUGE FOR BIOPSY NEEDLE

(75) Inventors: Nassir Navab, Plainsboro, NJ (US); Bernhard Geiger, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 08/722,724

(22) Filed: Sep. 30, 1996

(51) Int. Cl.
*A61B 5/05* (2006.01)
(52) U.S. Cl. ..................... 600/407; 606/130
(58) Field of Classification Search ............ 128/653.1; 606/130; 378/20, 205, 207, 208; 600/407, 600/425
See application file for complete search history.

(56) References Cited

U.S. PATENT DOCUMENTS

| 4,608,977 | A | * | 9/1986 | Brown .................... 128/303 B |
| 4,638,798 | A | | 1/1987 | Shelden et al. ......... 128/303 B |
| 4,750,487 | A | | 6/1988 | Zanetti ................... 128/303 B |
| 4,883,053 | A | | 11/1989 | Simon .................... 128/303 B |
| 4,923,459 | A | * | 5/1990 | Nambu ....................... 606/130 |
| 4,930,525 | A | | 6/1990 | Palestrant .................... 128/896 |
| 4,979,815 | A | | 12/1990 | Tsikos ............................ 356/1 |
| 5,147,372 | A | * | 9/1992 | Nymark et al. ............. 606/130 |
| 5,154,723 | A | * | 10/1992 | Kubota et al. .............. 606/130 |
| 5,163,430 | A | * | 11/1992 | Carol ....................... 128/653.1 |
| 5,176,689 | A | * | 1/1993 | Hardy et al. ................ 606/130 |
| 5,189,690 | A | | 2/1993 | Samuel ........................ 376/162 |
| 5,201,742 | A | | 4/1993 | Hasson ........................ 606/130 |
| 5,219,351 | A | * | 6/1993 | Teubner et al. ............. 606/130 |
| 5,221,283 | A | | 6/1993 | Chang .......................... 606/130 |
| 5,330,485 | A | * | 7/1994 | Clayman et al. ............ 606/130 |
| 5,368,015 | A | | 11/1994 | Wilk ............................... 128/4 |
| 5,383,454 | A | * | 1/1995 | Bucholz .................. 128/653.1 |
| 5,387,220 | A | | 2/1995 | Pisharodi ..................... 606/130 |
| 5,389,101 | A | | 2/1995 | Heilbrun et al. ............ 606/130 |
| 5,398,684 | A | | 3/1995 | Hardy ...................... 128/653.1 |
| 5,452,720 | A | * | 9/1995 | Smith et al. ............. 128/653.1 |
| 5,474,564 | A | * | 12/1995 | Clayman et al. ............ 606/130 |
| 5,551,429 | A | * | 9/1996 | Fitzpatrick et al. ....... 128/653.1 |
| 5,584,292 | A | | 12/1996 | Cheung .................... 128/653.1 |

(Continued)

FOREIGN PATENT DOCUMENTS

WO        WO 91/07922        *   6/1991   ................. 606/130

(Continued)

*Primary Examiner*—Eleni Mantis Mercader
(74) *Attorney, Agent, or Firm*—Michele L. Conover

(57) ABSTRACT

Apparatus for determining a proper insertion depth of a biopsy needle to be inserted at a selected point on the body of a patient so that a sampling end of the needle just reaches to a designated target area within the body, comprises at least one straight calibrated pointing device, having a pivot point at one end thereof, and aligned to point through the selected point in a straight line passing through the designated target region, an image of the pointing device being formed on each of first and second image planes by utilizing radiation from respective first and second radiation source positions, along with images corresponding to the selected point and the target area. Needles are provided for casting an image on one at least one of the image planes, the needles being pivotably mounted at a further pivot point different from the pivot point of the pointing device and being constrained for movement in plane defined by the pivot point, the further pivot point and by the pointing device.

25 Claims, 19 Drawing Sheets

U.S. PATENT DOCUMENTS

| | | | |
|---|---|---|---|
| 5,609,152 A | 3/1997 | Pellegrino et al. | 128/653.1 |
| 5,618,288 A * | 4/1997 | Calvo | 606/130 |
| 5,628,327 A | 5/1997 | Unger et al. | 128/749 |
| 5,634,929 A * | 6/1997 | Misko et al. | 606/130 |
| 5,638,819 A * | 6/1997 | Manwaring et al. | 128/653.1 |
| 5,647,373 A | 7/1997 | Paltieli | 128/749 |
| 5,662,111 A * | 9/1997 | Cosman | 128/653.1 |
| 5,682,892 A * | 11/1997 | Selder et al. | 128/653.2 |
| 5,695,501 A * | 12/1997 | Carol et al. | 606/130 |
| 5,748,767 A * | 5/1998 | Raab | 382/128 |

FOREIGN PATENT DOCUMENTS

| | | | | |
|---|---|---|---|---|
| WO | WO 92/00702 | * | 1/1992 | 606/130 |

* cited by examiner

TRIGONOMETRIC DEPTH GAUGE FOR BIOPSY NEEDLE

The present invention relates to a system, apparatus, and method for accurate positioning of a surgical tool, such as a biopsy needle, with respect to a deep seated target inside a patient and, more specifically, a positioning device that takes as its input a needle entry point and a target point selected on the screen of a fluoroscope for automatically positioning a needle guide and indicating the depth to the target point.

The subject matter of the following copending patent applications being filed on even date herewith is closely related to the subject matter of the present application and is incorporated herein by reference to the extent it is not incompatible with the present disclosure APPARATUS AND METHOD FOR POSITIONING A BIOPSY NEEDLE Ser. No. 08/722,725, APPARATUS AND METHOD FOR AUTOMATICALLY POSITIONING A BIOPSY NEEDLE Ser. No. 08/722,707, and APPARATUS AND METHOD FOR DETERMINING THE CORRECT INSERTION DEPTH FOR A BIOPSY NEEDLE Ser. No. 08/722,708. All are filed in the names of Navab and Geiger, the present inventors, and all are assigned to Siemens Corporate Research, Inc., as is the present application.

Needle biopsy is one of the most frequent surgical interventions. Typically, a fine needle is used to remove tissue portions from a lesion inside the body. If the lesion is very small and is deep-seated within the body or is not palpable, the surgeon needs guidance in order to make sure that the tip of the needle reaches the desired location.

Currently used image based guidance methods include the following. Ultrasound (US), X-ray fluoroscopy, CT fluoroscopy, and CT/MRI in combination with real time registration tools. The first three methods provide real time intra-operative images of the patient and enable the surgeon to see the needle as it approaches the target.

Ultrasound is relatively inexpensive and is a readily available image modality. However, its usage for guidance is limited to lesions that are close to the skin and that show a well defined signal.

The X-ray fluoroscope is a widely available, low cost two-dimensional (2D) imaging equipment. Since it shows a two-dimensional projection, two (generally orthogonal) views are necessary in order to determine the biopsy needle position. This can be done by turning the arm of a simple fluoroscope, such as a C-arm fluoroscope, an example of which is shown in FIG. 1, or by using a fluoroscope such as that illustrated in FIG. 2 that provides two simultaneous orthogonal views. Since the needle has to be manipulated in the image field, one cannot avoid a X-ray exposure of the physician when using such techniques. As is well-known, unnecessary exposure of health workers to X-ray radiation is believed to be hazardous to health and it is desirable that it should be avoided to the extent possible.

CT-Fluoroscopy permits real-time display of CT images. The physician controls X-ray exposure during continuous tube rotation. The exact position of the needle can be traced by moving the table. In the case for CT-Fluoroscopy also, the surgeon is exposed to X-rays.

CT/MRI in combination with real time registration tools is based on pre-operative 3-D data acquisition (CT or MRI). The lesion is outlined in the resulting dataset. During the actual biopsy, the position and orientation of the patient and the needle have to be known precisely and aligned with the pre-operative data.

Therefore two registrations have to be used for guiding the needle: the pre-operative data showing the lesion has to be registered with the patient. This can be done by attaching invariant markers to the patient (stereo-tactic frames) before data acquisition or by matching invariant patient features, such as the skull or bones.

The needle has to be registered with the patient. One possibility is to attach optical markers to the needle which can be tracked by a system of cameras or by X-ray fluoroscopy, or to use mechanical devices like passive robot arms that register the position of the needle at any moment. This technique requires highly specialized and costly 3-D imaging facilities that are typically only available at a few research sites. Despite the image guidance, a successful biopsy procedure still depends on the manual skills and judgement of the surgeon who is manipulating the needle.

There is a need herein recognized for an alignment device that is adjustable to the right direction and that indicates the distance to a deep-seated target. Among the benefits that result from such a device are acceleration of the procedure, increase of the safety of the procedure, and reduction of radiation exposure for both the patient and for the surgeon.

In accordance with the objects of the present invention, an X-ray image guided system provides assistance in the execution of needle biopsy. It can also be used for minimal access surgical procedures, known as "keyhole surgery". One of the objects of the present system, which is simple and readily implemented, is to help surgeons overcome difficulties associated with positioning the biopsy needle or performing minimally invasive surgery in three dimensions while utilizing two-dimensional images for guidance in the procedure.

Another object of the present invention is to practically eliminate or reduce to a minimum the need for a surgeon's reliance on a radiologist to open an access track pre-operatively in the radiology suite.

Furthermore, another object of the invention is to practically eliminate the need for accurate geometrical calibration. The present invention is believed to provide a first opportunity in which quantitative imaging guidance is made possible without a dedicated geometrical calibration procedure.

The invention permits the accurate positioning of a surgical tool, such as biopsy needle, with respect to a deep seated target inside a patient. It is the practical application of an algorithm in accordance with the invention which makes the accurate positioning possible.

In accordance with the invention, the depth of a deep-seated target within a patient's body is readily computed from one single radiographic image. Based on geometrical reasoning involving a mechanical device, simple in conception, in accordance with the invention, biopsy needles may be considered in the context of the invention as an adjunct to traditional medical imaging systems such as C-arm equipment and fluoroscopes.

Generally, a preferred position for a biopsy needle from the surgical point of view is a position above the patient from which it goes through the organ of interest. In addition, the surgeon needs to know the depth of the target in order to correctly insert the needle.

In accordance with an aspect of the invention, apparatus for determining the required insertion depth for a biopsy needle priorly aligned for proper insertion into the body of a patient at a selected point on a surface of the body, so as to enter in a straight line passing through a designated target region within the body by the use of first and second image planes, such that at the proper depth, an end of the needle just reaches the target area, comprises: a base portion including a circle portion having a center point; a planar semicircular portion mounted onto the base portion such that the diameter of the semicircular portion is concentric with the center point and rotatable thereabout, the semicircle portion being further rotatable about a straight line through the diameter; a straight pointing device having one end thereof pivotably affixed to the center point and being constrained for movement within a plane defined by the planar semicircular portion; and at least one straight pointing needle having one end thereof pivotably affixed at one end of the diameter of the semicircular portion and being constrained for movement within a plane defined by the planar semicircular portion.

In accordance with another aspect of the invention, apparatus for determining the required insertion depth for a biopsy needle includes apparatus for measuring an angle $\Theta$ of the plane defined by the semicircular portion relative to the base portion, an angle $\phi$ of the pointing device relative to the base portion, and an angle $\phi_1$ defined by the at least one pointing needle relative to the base portion.

In accordance with another aspect of the invention, apparatus for determining the required insertion depth for a biopsy needle includes a further pointing needle having one end thereof pivotably affixed at the other end of the diameter of the semicircular portion and being constrained for movement within the plane defined by the planar semicircular portion.

In accordance with an aspect of the invention, at least one of the pointing needles is made of relatively radiation-transparent material.

In accordance with another aspect of the invention, at least one of the pointing needles is made of relatively radiation-transparent material and includes imbedded therein radiation-opaque markers.

In accordance with another aspect of the invention, the depth is obtained by solving the equation $$AC = \sin(\phi_1) \times \frac{AB}{\sin(\phi_1 - \phi)}$$

In accordance with another aspect of the invention, apparatus for determining the required insertion depth for a biopsy needle priorly aligned for proper insertion into the body of a patient at a selected point on a surface of the body, so as to enter in a straight line passing through a designated target region within the body by the use of first and second image planes, such that at the proper depth, an end of the needle just reaches the target area, comprises: a base including a first planar measuring portion having a center point; a second planar measuring portion mounted onto the base portion such that a center point of the second measuring portion is concentric with the center point of the first planar measuring portion so that the second planar measuring portion is rotatable about the center point, the second planar measuring portion being further rotatable about a straight line through its center; and an essentially straight pointing device having one end thereof pivotably affixed to the center point and being constrained for movement within a plane defined by the planar semicircular portion; and at least one essentially straight pointing needle having one end thereof pivotably affixed at one end of the straight line of the semicircular portion and being constrained for movement within a plane defined by the planar semicircular portion.

In accordance with another aspect of the invention, apparatus for determining a proper insertion depth of a biopsy needle to be inserted at a selected point on the body of a patient so that a sampling end of the needle just reaches to a designated target area within the body, comprises: at least one straight calibrated pointing device, having a pivot point at one end thereof, and aligned to point through the selected point in a straight line passing through the designated target region, an image of the pointing device being formed on each of first and second image planes by utilizing radiation from respective first and second radiation source positions, along with images corresponding to the selected point and the target area; and needle apparatus for casting an image on one at least one of the image planes, the needle apparatus being pivotably mounted at a further pivot point different from the pivot point of the pointing device and being constrained for movement in plane defined by the pivot point, the further pivot point and by the pointing device.

In accordance with another aspect of the invention, apparatus for determining a proper insertion depth of a biopsy needle to be inserted at a selected point on the body of a patient so that a sampling end of the needle just reaches to a designated target area within the body, comprises at least one straight calibrated pointing device pivoted at one end thereof at a pivot point; positioning apparatus for automatically positioning or aligning the at least one straight calibrated pointing device as a guide for a biopsy needle for proper insertion into the body of a patient from a selected point on a surface of the body, so as to enter in a straight line passing through a designated target region within the body, in conjunction with an imaging system utilizing radiation from a first source position for deriving a first radiographic image on a first image plane of a portion of the body including a first image of the selected point and a first image of the target region, the first source position, the first image of the selected point, and the first image of the target region defining a first viewing plane $\pi$, the imaging system utilizing radiation from a second source position for deriving a second radiographic image on a second image plane of the portion of the body, including a second image of the selected point and a second image of the target region, the second source position, the second image of the selected point, and the second image of the target region defining a second viewing plane $\pi'$, the positioning apparatus comprising: measurement apparatus for determining an angle $\Theta_1$ for a selected first auxiliary plane and an angle $\Theta_2$ for a selected second auxiliary plane with respect to a selected set of coordinates and for storing the angles, the second plane angle being different from the first plane angle such that the first and second auxiliary planes form an intersection line; apparatus for constraining the calibrated pointing device for moving rotatably about the selected point and within the first auxiliary plane to a first angle of inclination $\phi_1$ relative to sa set of coordinates and for controlling the calibrated pointing device such that a projection or extension of an image of the calibrated pointing device on the first image plane passes through the first image of the target region and for storing the angle $\phi_1$, the alignment and control apparatus further controlling the calibrated pointing device for moving rotatably about the selected point and within the second auxiliary plane to a second angle of inclination $\phi_2$ relative to the set of coordinates such that a projection or extension of an image of the calibrated pointing device on the second image plane passes through the second image of the target region and for storing the angle $\phi_2$, whereby the first viewing plane $\pi$ is uniquely defined by the angles $\Theta_1$, $\Theta_2$, $\phi_1$, and $\phi_2$ relative to the set of coordinates; apparatus for determining orientation angles $\alpha$ and $\Theta_3$ of the viewing plane $\pi$ from stored values of the angles $\Theta_1$, $\Theta_2$, $\phi_1$, and $\phi_2$, and storing the angles $\alpha$ and $\Theta_3$; and apparatus for moving the calibrated pointing device rotatably about the selected point and within the first viewing plane π, as defined by the angles α and $\Theta_3$, to a third angle of inclination $\phi_3$ relative to the set of coordinates such that a projection or extension of an image of the calibrated pointing device on the second image plane passes through the further image of the target region, whereby the pointer points directly through the selected point toward the target region, such that that respective images of pointing device are formed on the first and second image planes, along with images corresponding to the selected point and the target area; and needle apparatus for casting an image on one at least one of the image planes, the needle apparatus being pivotably mounted at a further pivot point different from the pivot point of the pointing device and being constrained for movement n plane defined by the pivot point, the further pivot point and by the pointing device.

In accordance with another aspect of the invention, a method for determining the required insertion depth for a biopsy needle so as to just reach a selected target area within a body, wherein a proper direction for insertion of the biopsy needle has been priorly determined from a radiographic image on a viewing plane such that an extension of the direction of the biopsy needle from a selected insertion point into the body in a straight line leads through a selected target area, comprises the steps of: defining a plane containing the biopsy needle; adjusting a pointing needle, pivoted at one end and constrained to move within the plane, until a prologation of the line of an image of the pointing needle on the plane intersects the selected target area; and calculating the required insertion depth from knowledge of a base line length AC joining the pivot point and the selected insertion point and respective angles, $\phi$ and $\phi_1$, of the biopsy needle and the pointing needle.

In accordance with another aspect of the invention, the required insertion depth for a biopsy needle in accordance with claim 17 wherein the required insertion depth is given by $$AC = \sin(\phi_1) \times \frac{AB}{\sin(\phi_1 - \phi)}$$

In accordance with another aspect of the invention, apparatus for determining the required insertion depth for a biopsy needle priorly aligned for proper insertion into the body of a patient at a selected point on a surface of the body, so as to enter in a straight line passing through a designated target region within the body by the use of first and second image planes, such that at the proper depth, an end of the needle just reaches the target area, the apparatus comprising: a base portion including a circle portion having a center point; a planar semicircular portion mounted onto the base portion such that the diameter of the semicircular portion is concentric with the center point and rotatable thereabout, the semicircle portion being further rotatable about a straight line through the diameter; a straight pointing device having one end thereof pivotably affixed to the center point and being constrained for movement within a plane defined by the planar semicircular portion; and first and second essentially straight pointing needles, each having one end thereof pivotably affixed at a respective end of the diameter of the semicircular portion and being constrained for movement within a plane defined by the planar semicircular portion.

In accordance with another aspect of the invention, apparatus for determining a proper insertion depth of a biopsy needle to be inserted at a selected point on the body of a patient so that a sampling end of the needle just reaches to a designated target area within the body, comprises at least one straight calibrated pointing device, having a pivot point at one end thereof, and aligned to point through the selected point in a straight line passing through the designated target region, an image of the pointing device being formed on each of first and second image planes by utilizing radiation from respective first and second radiation source positions, along with images corresponding to the selected point and the target area. Needles are provided for casting an image on one at least one of the image planes, the needles being pivotably mounted at a further pivot point different from the pivot point of the pointing device and being constrained for movement in plane defined by the pivot point, the further pivot point and by the pointing device.

The invention will be further understood from the detailed description of the prefered embodiments, in conjunction with the drawing in which.

Figure 4:
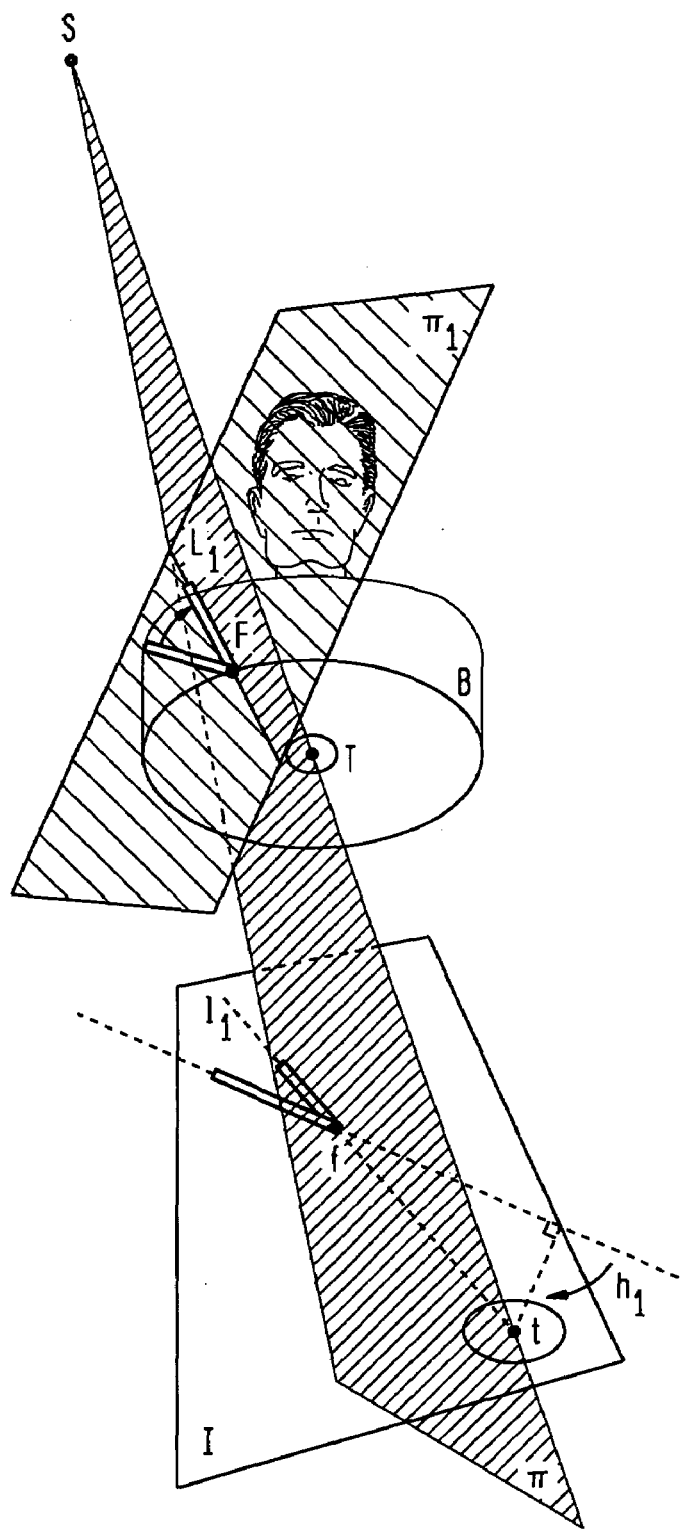
Figure 5:
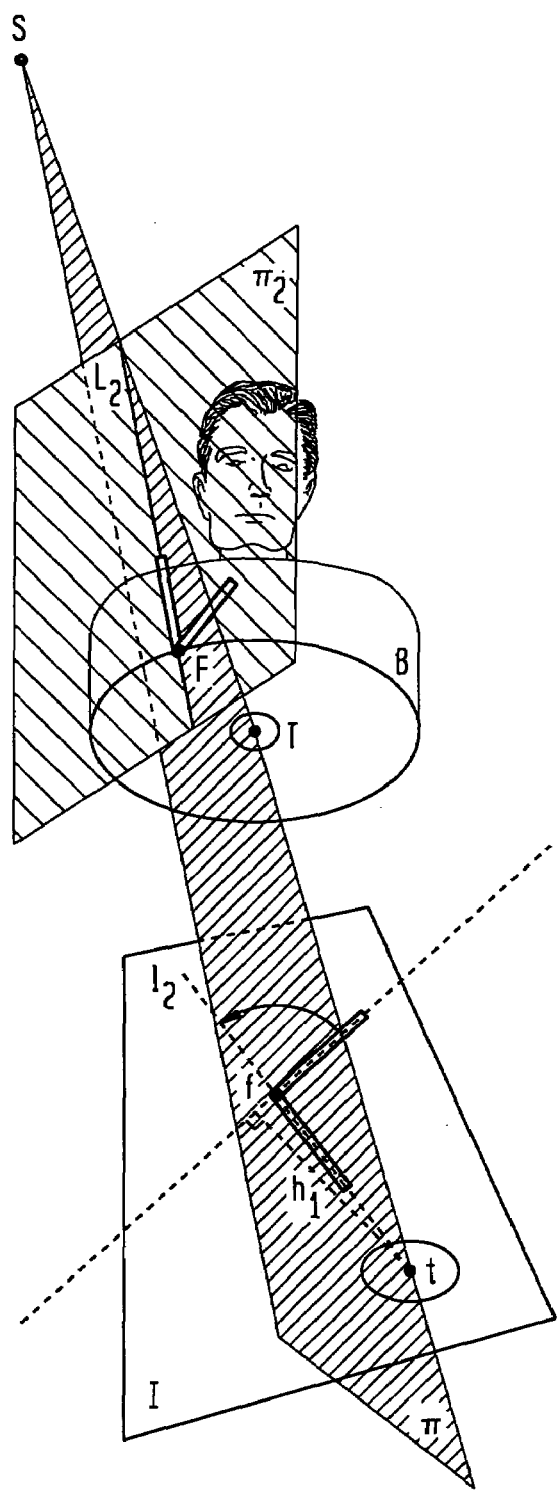
Figure 6:
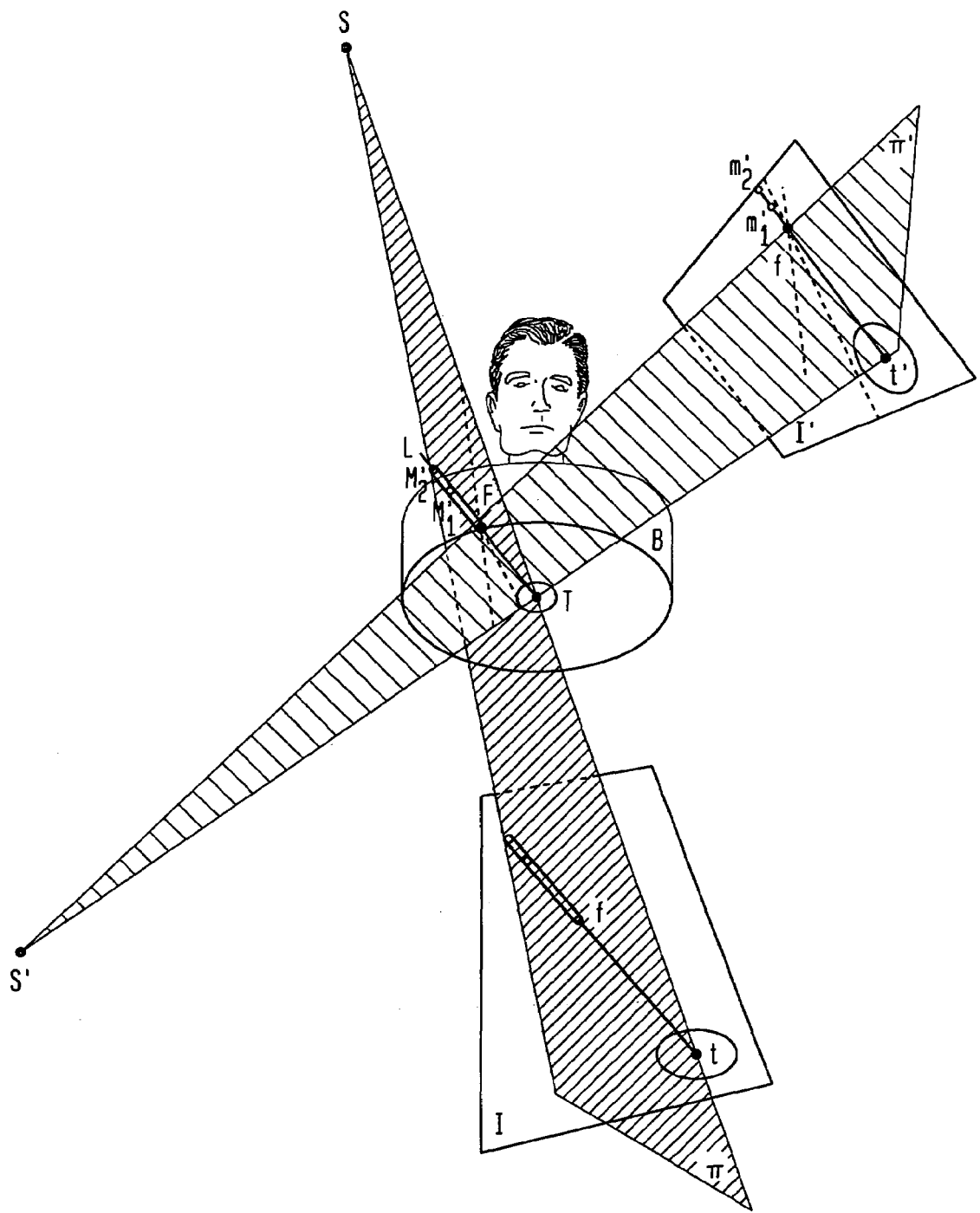
Figure 7:
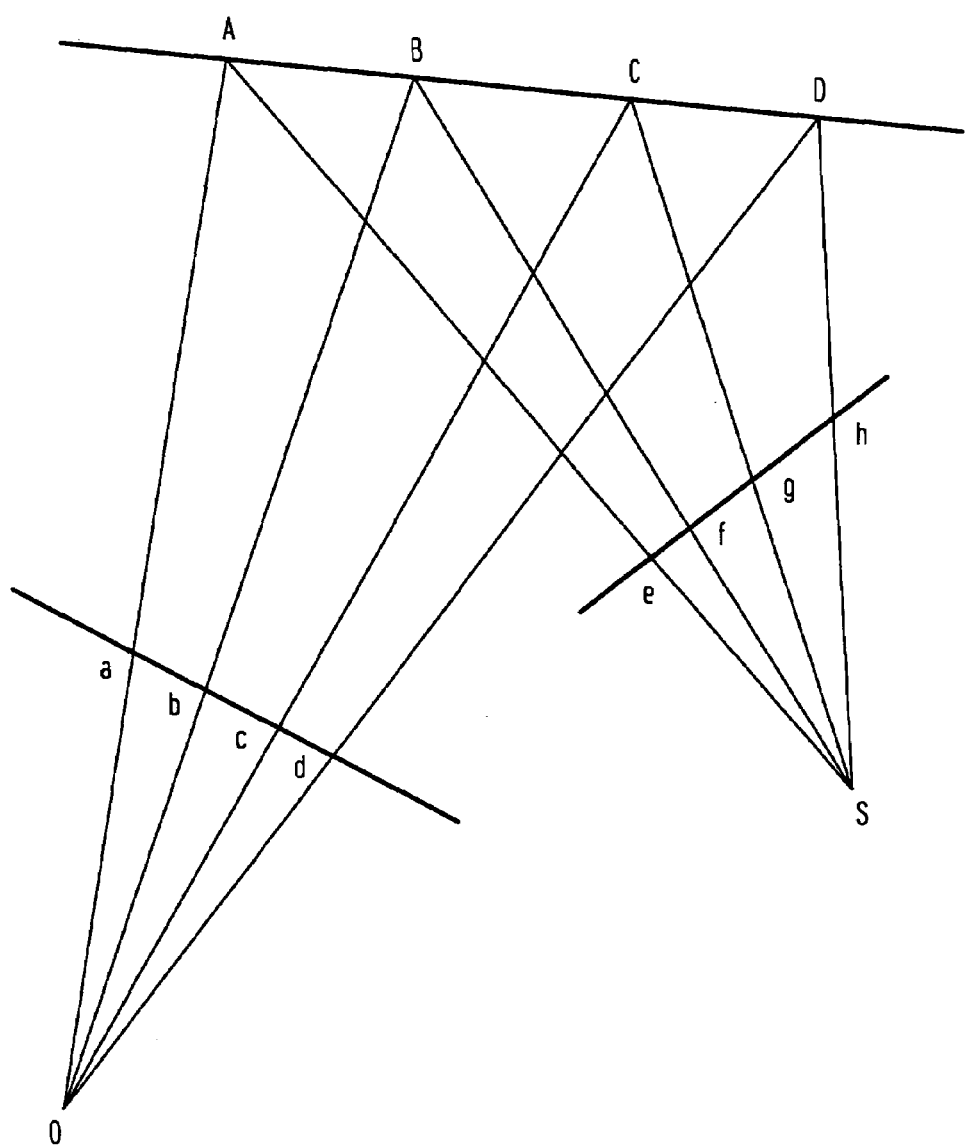
Figure 8:
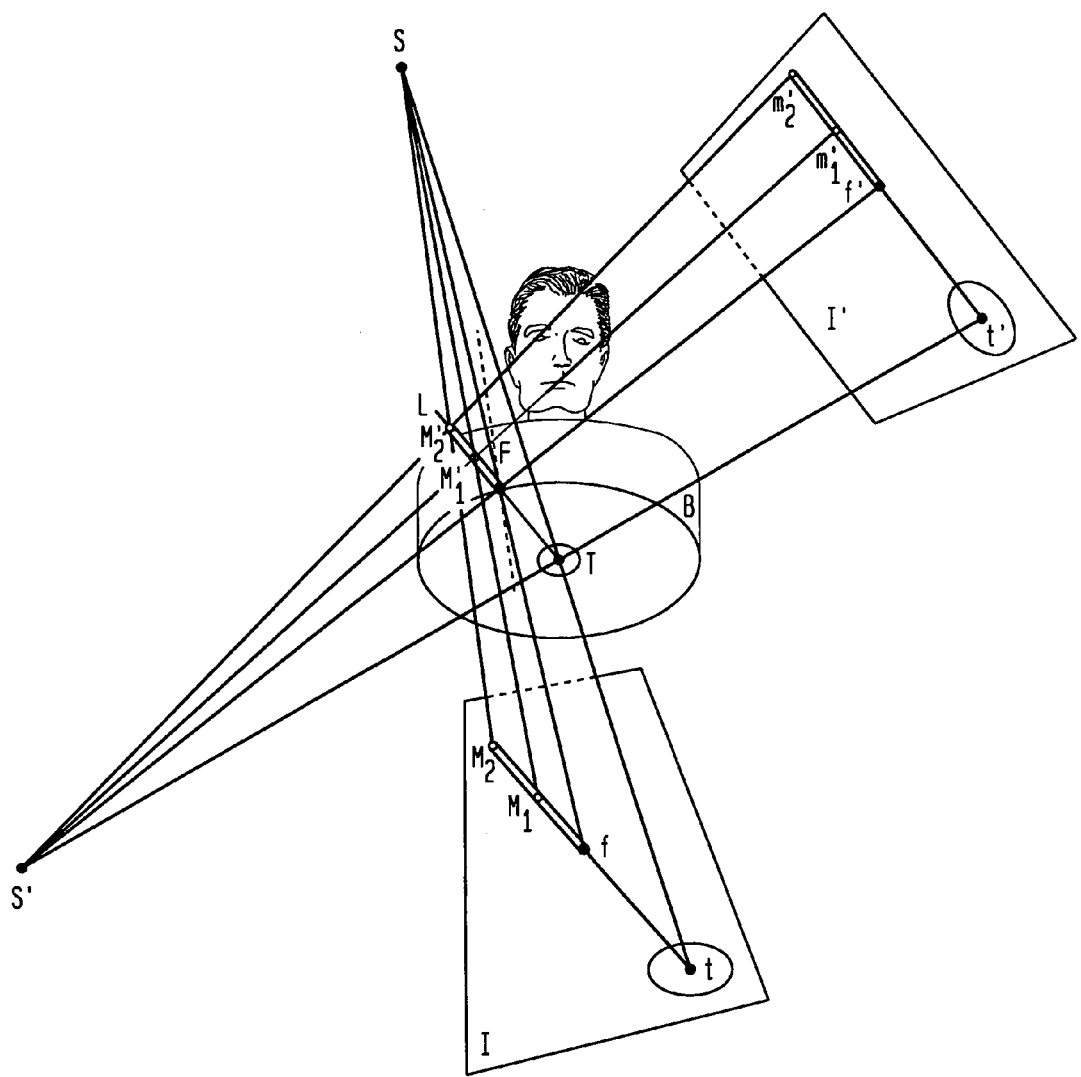
Figure 9:
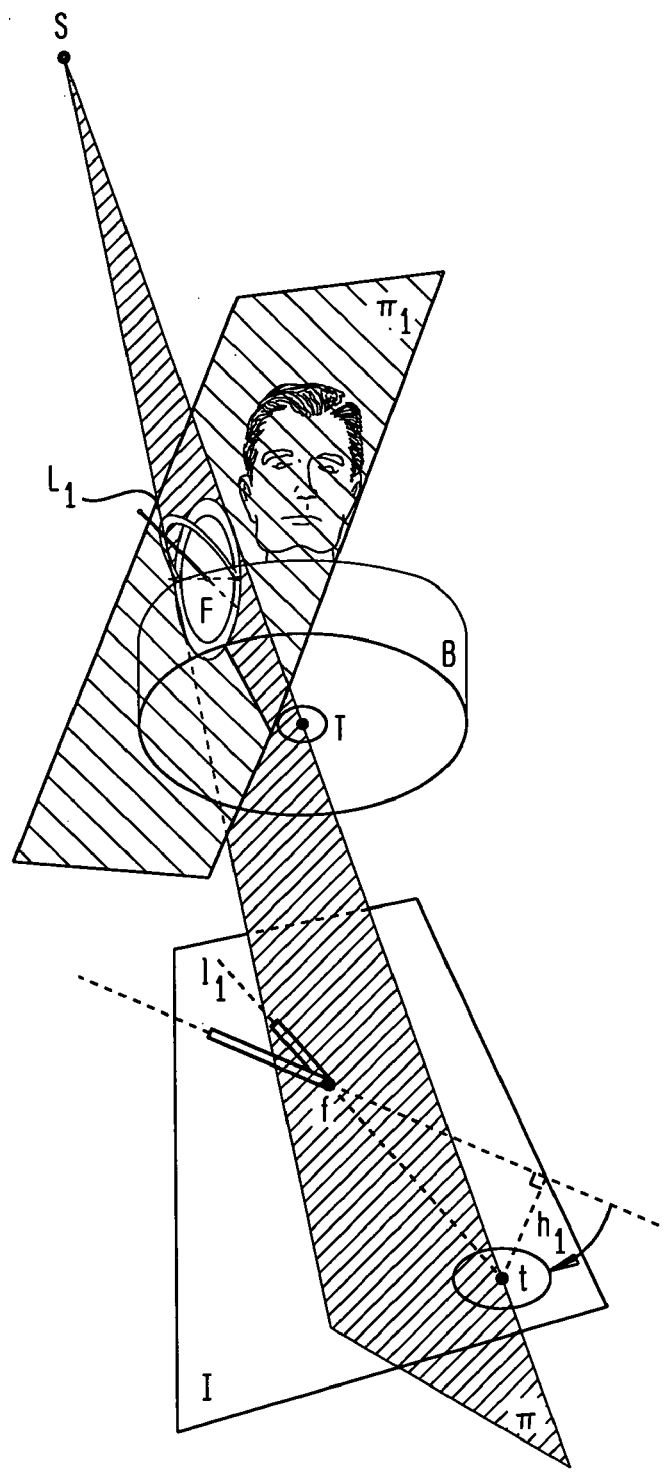
Figure 10:
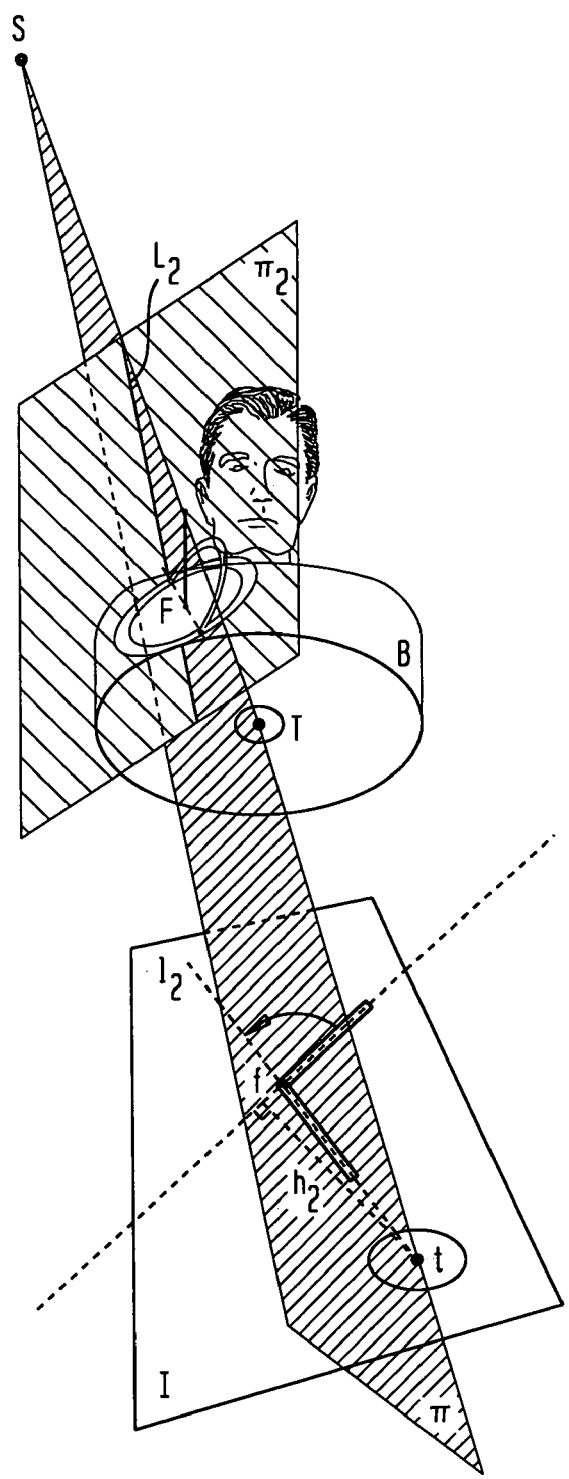
Figure 11:
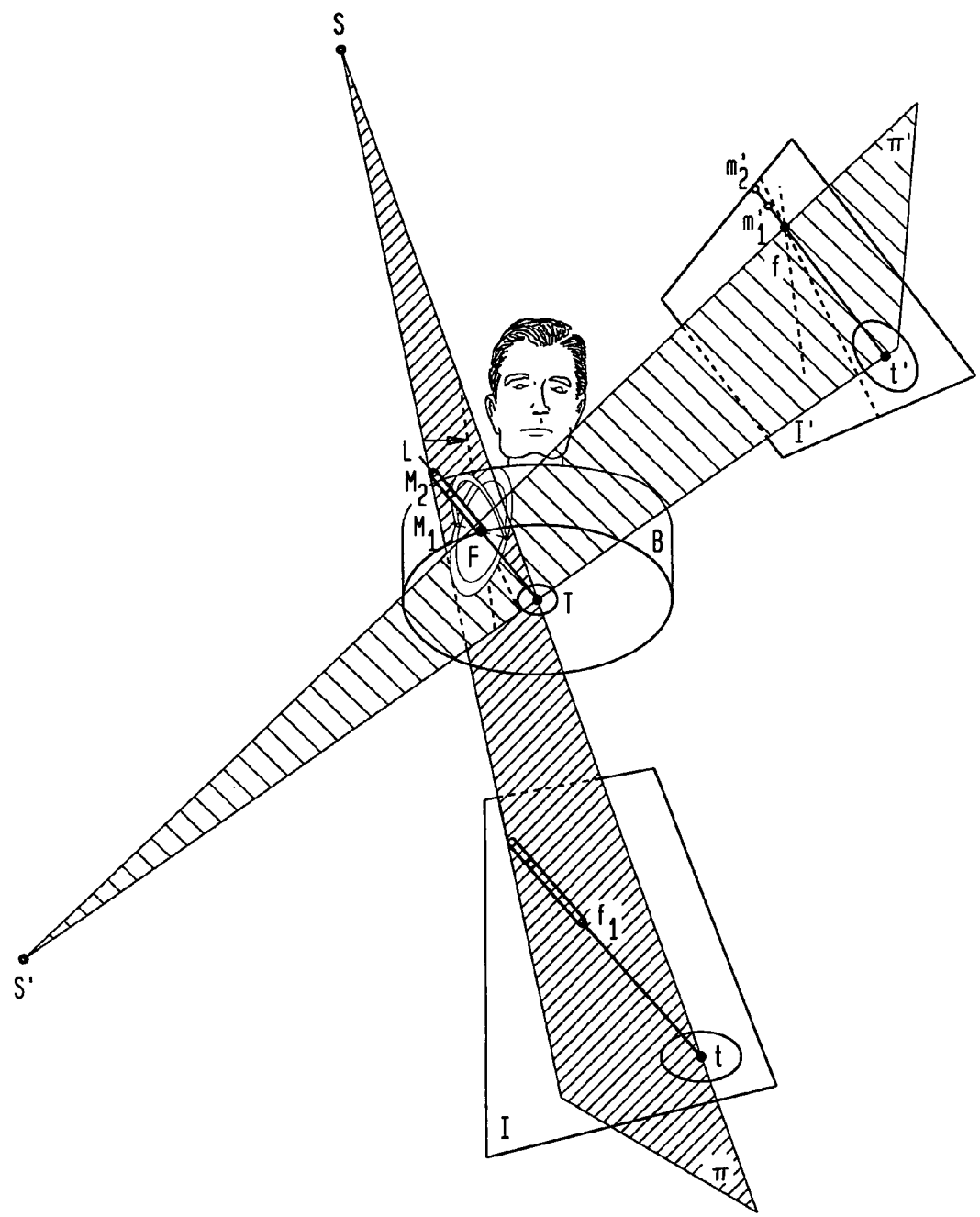
Figure 12:
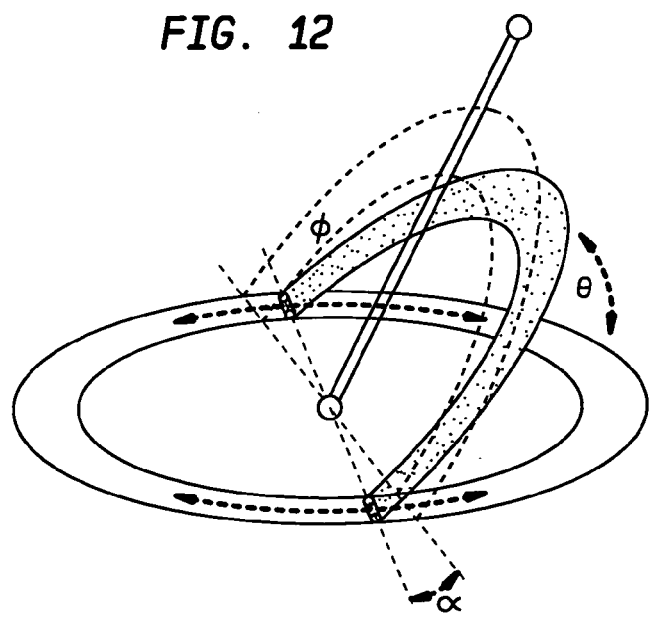
Figure 13:
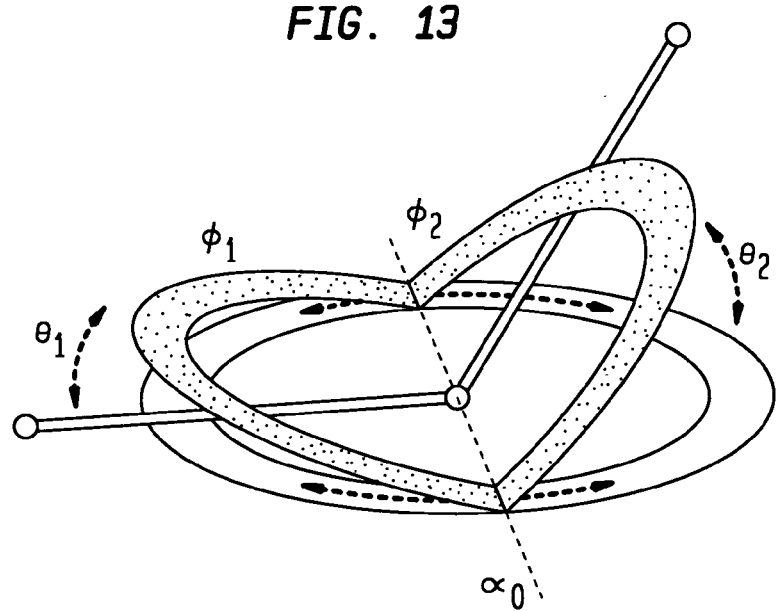
Figure 14:
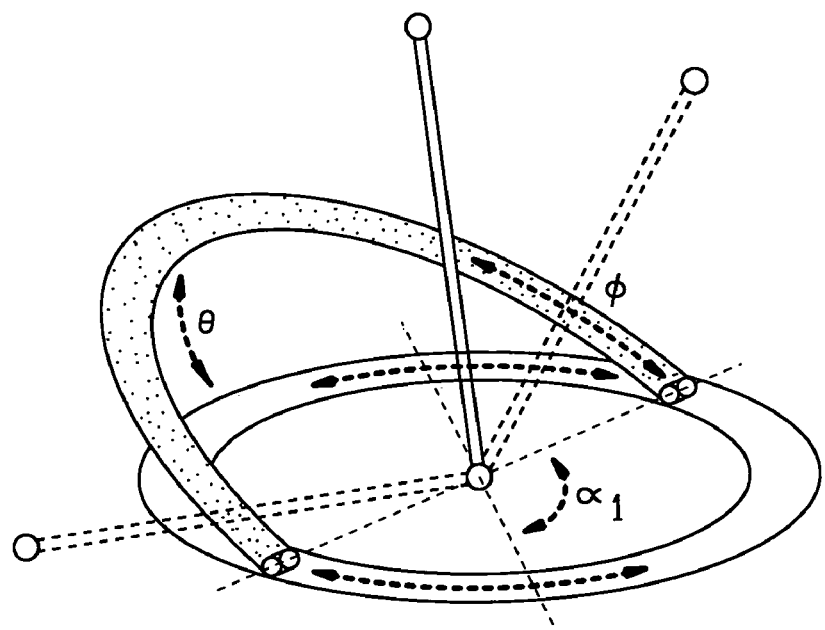
Figure 15:
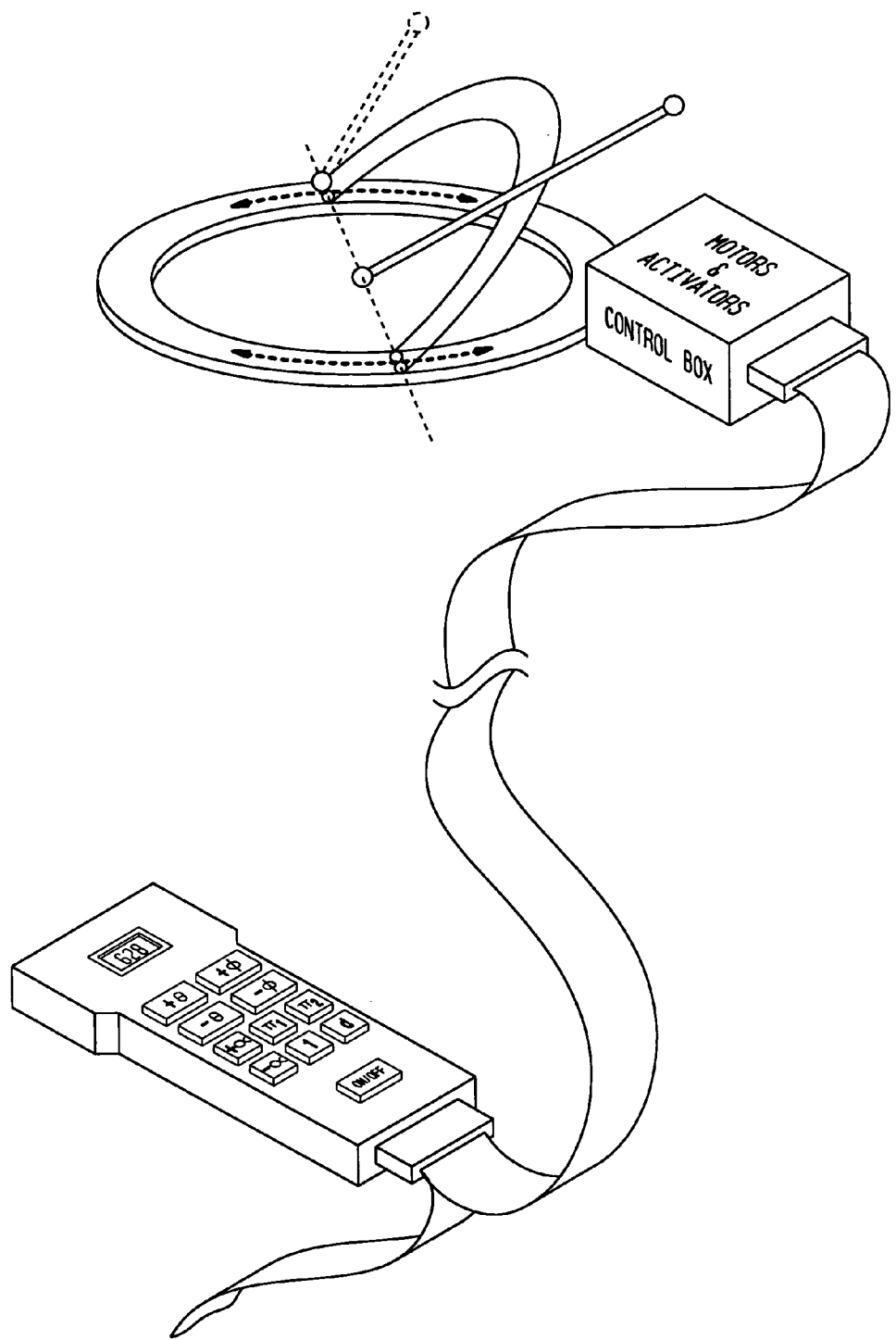
Figure 16:
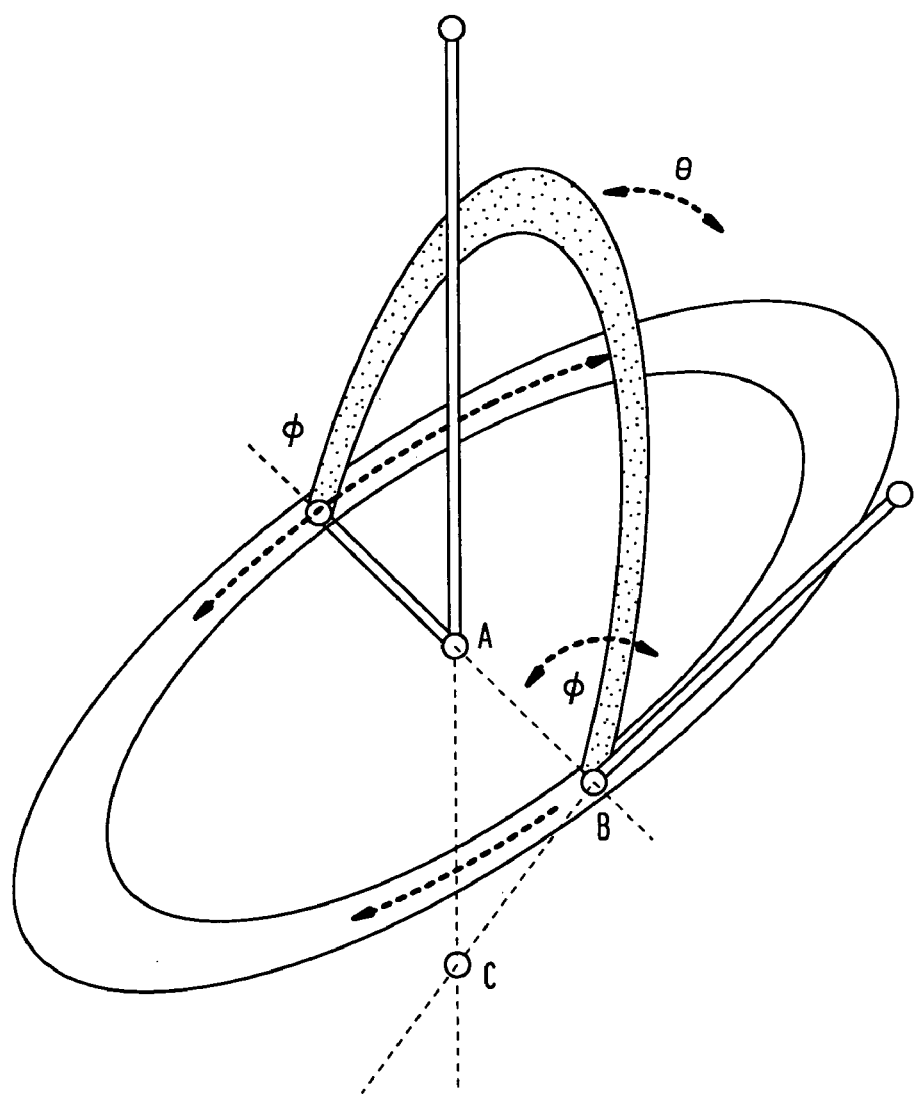
Figure 17:
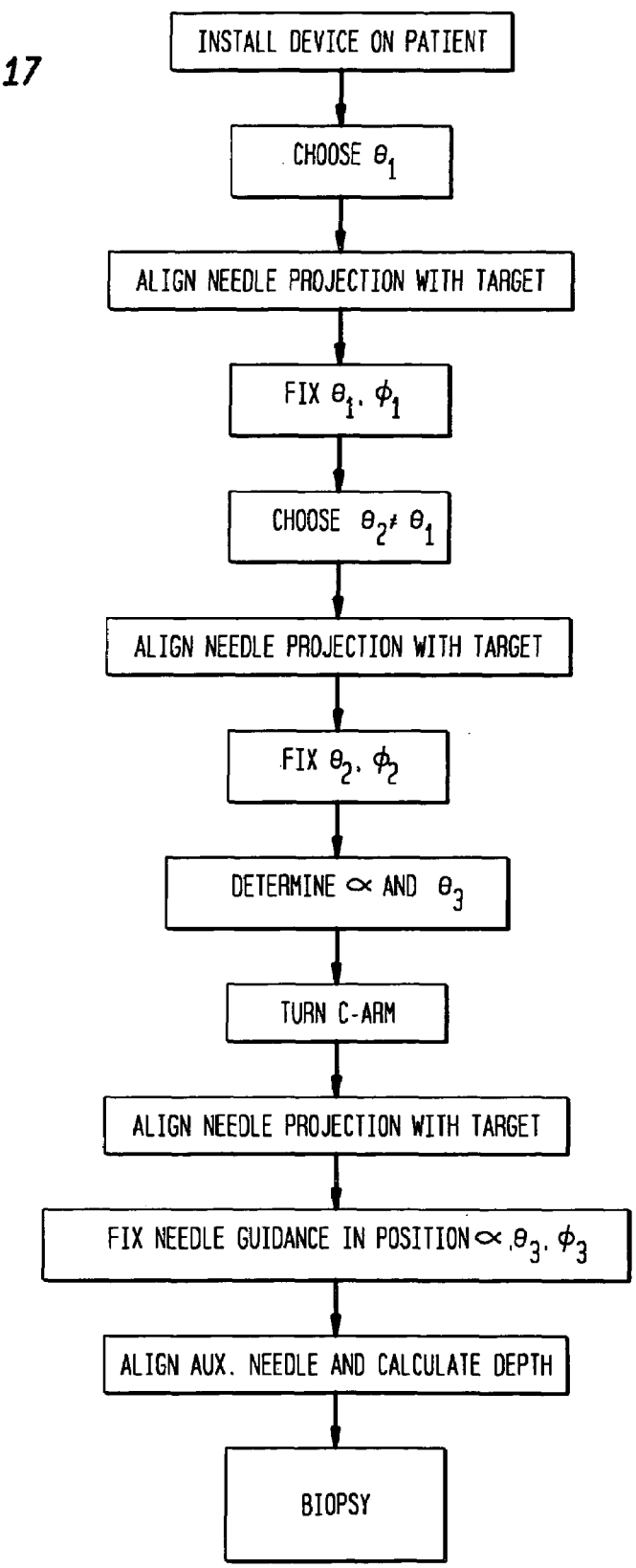
Figure 18:
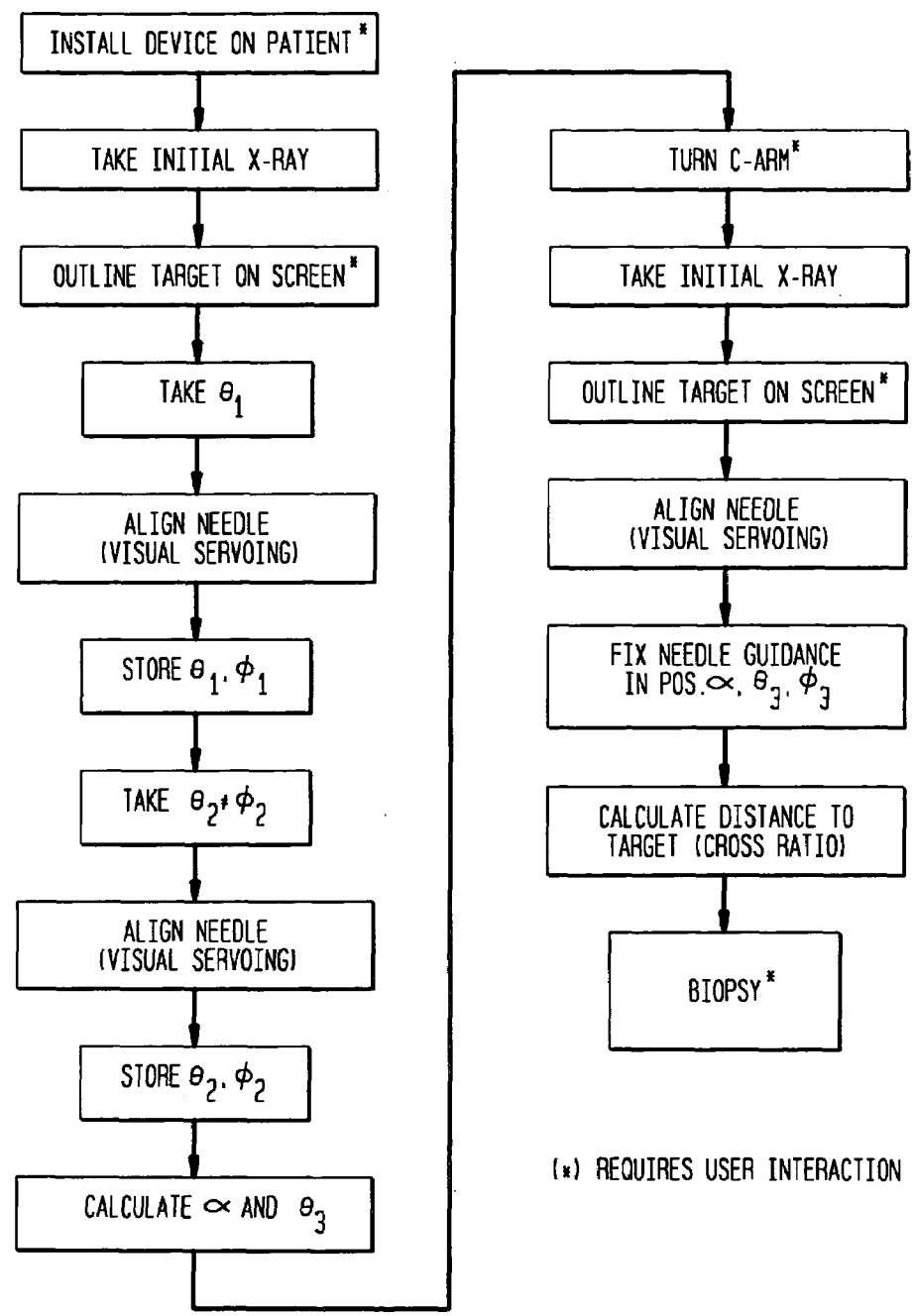
Figure 19:
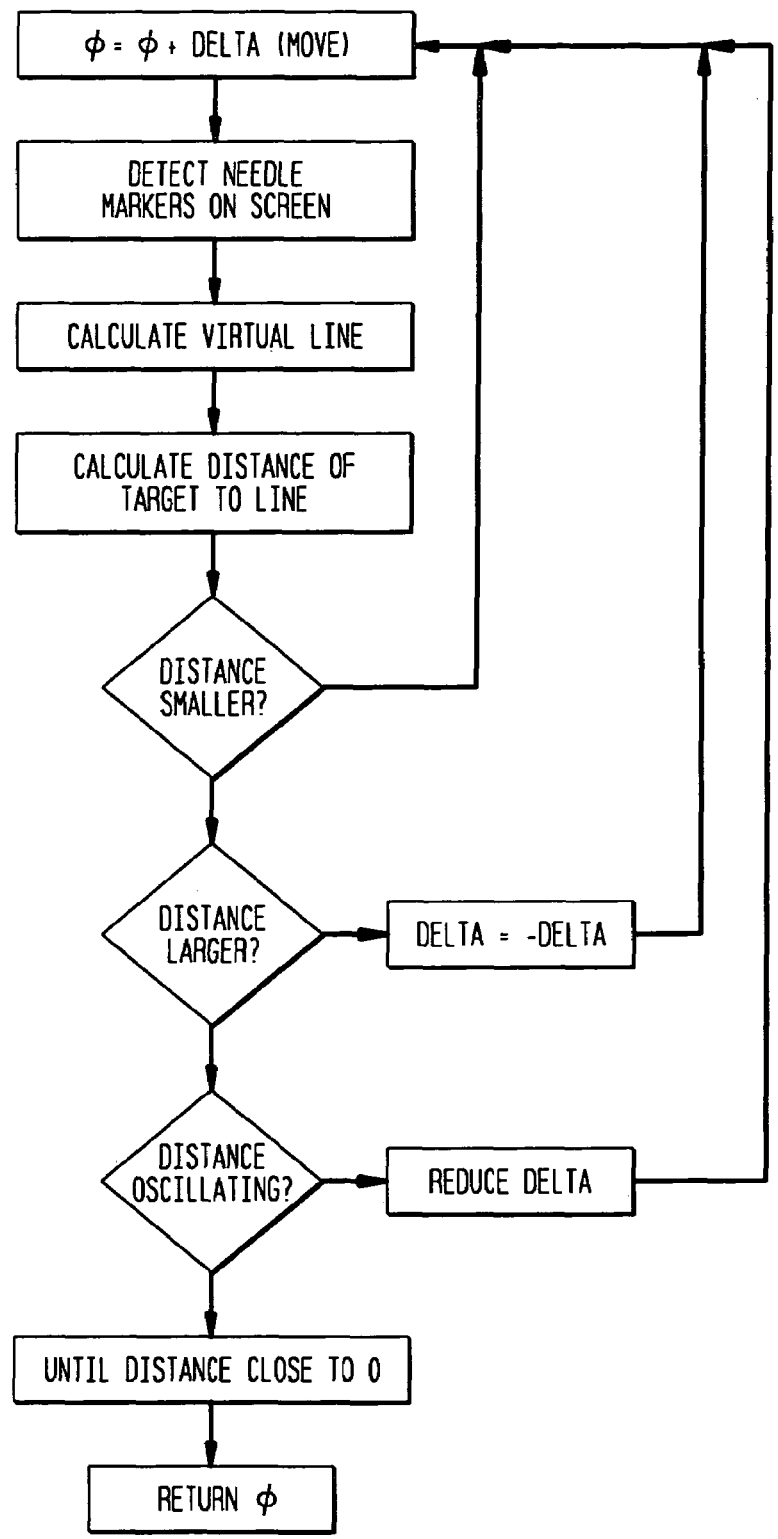
Figure 20:
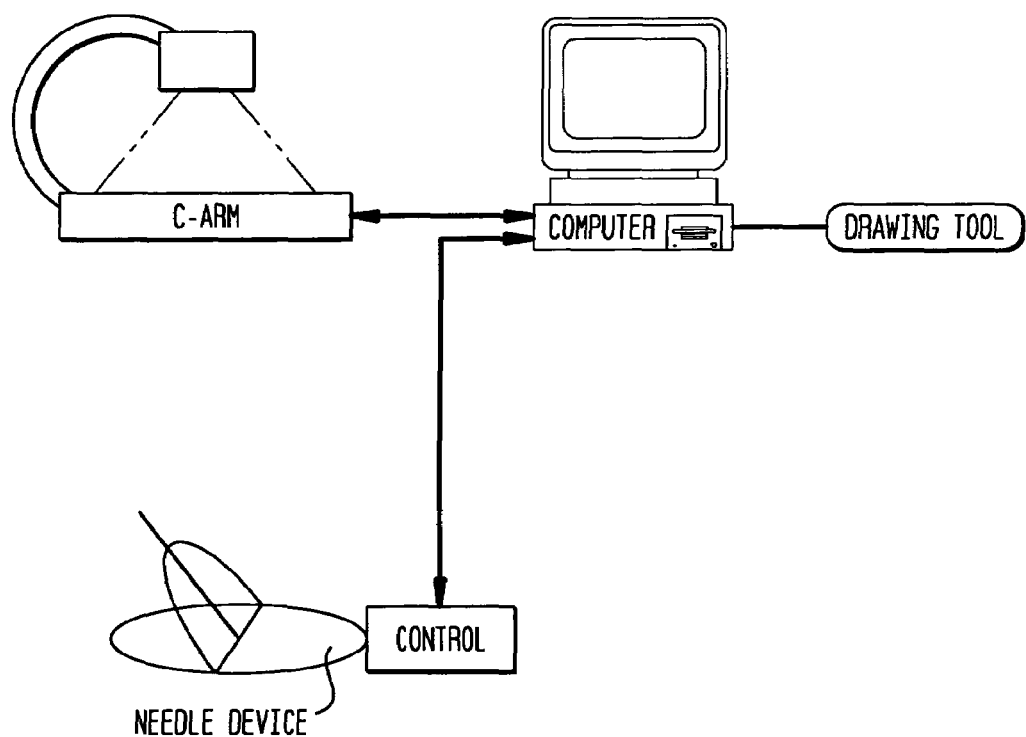

FIGS. 4, 5, and 6 show various steps of a method utilizable in conjunction with the invention;

FIGS. 7 and 8 show diagramatically apparatus and principles helpful to an understanding of the objects of the invention;

FIGS. 9, 10, and 11 show various steps of a method utilizable in conjunction with the invention;

FIGS. 12, 13, and 14 show diagramatic representations of apparatus utilizable in conjunction with the invention;

FIG. 15 shows a system diagram in accordance with the invention;

FIG. 16 a diagramatic representation of apparatus in accordance with the invention;

FIGS. 17, 18, and 19 show flow charts helpful to gaining an understanding of the invention;

FIG. 20 shows components of an automatic system and their interrelationship of a method utilizable in conjunction with the invention.

Apparatus and diagram drawings are not necessarily to scale.

Figure 1:
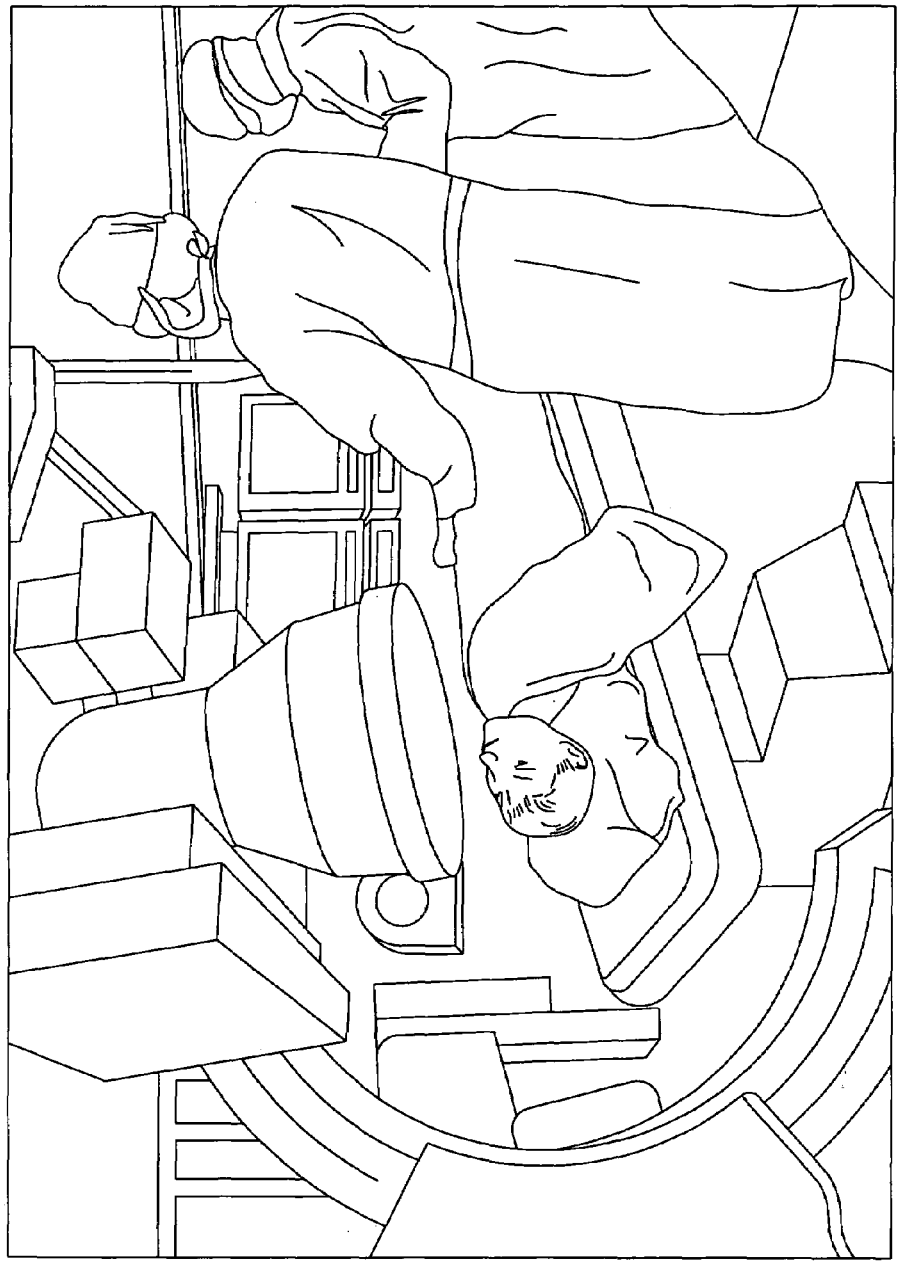
FIG. 1 shows a known type of C-arm fluoroscope, such as may be utilized in conjunction with the present invention.
Figure 2:
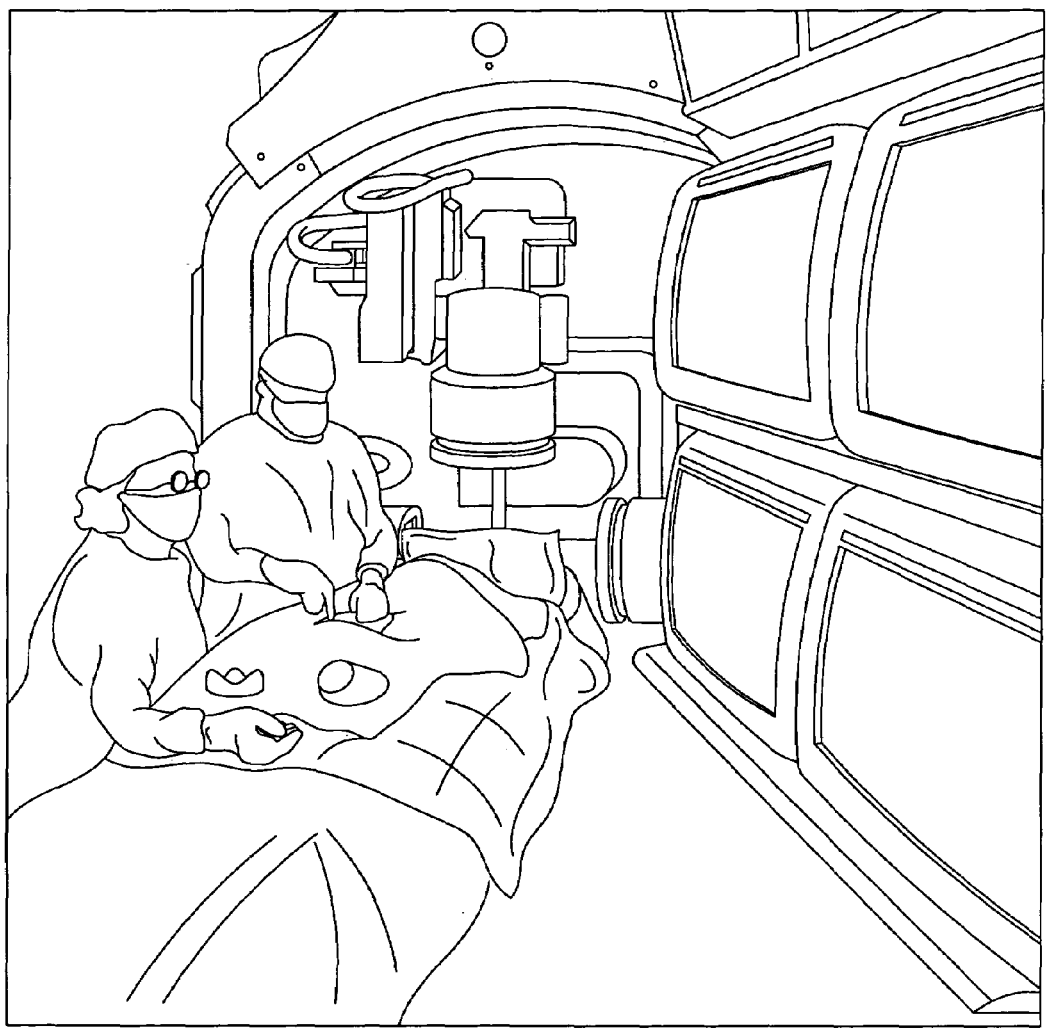
FIG. 2 shows a known type of fluoroscope with two simultaneous orthogonal views, such as may be utilized in conjunction with the present invention.
Figure 3:
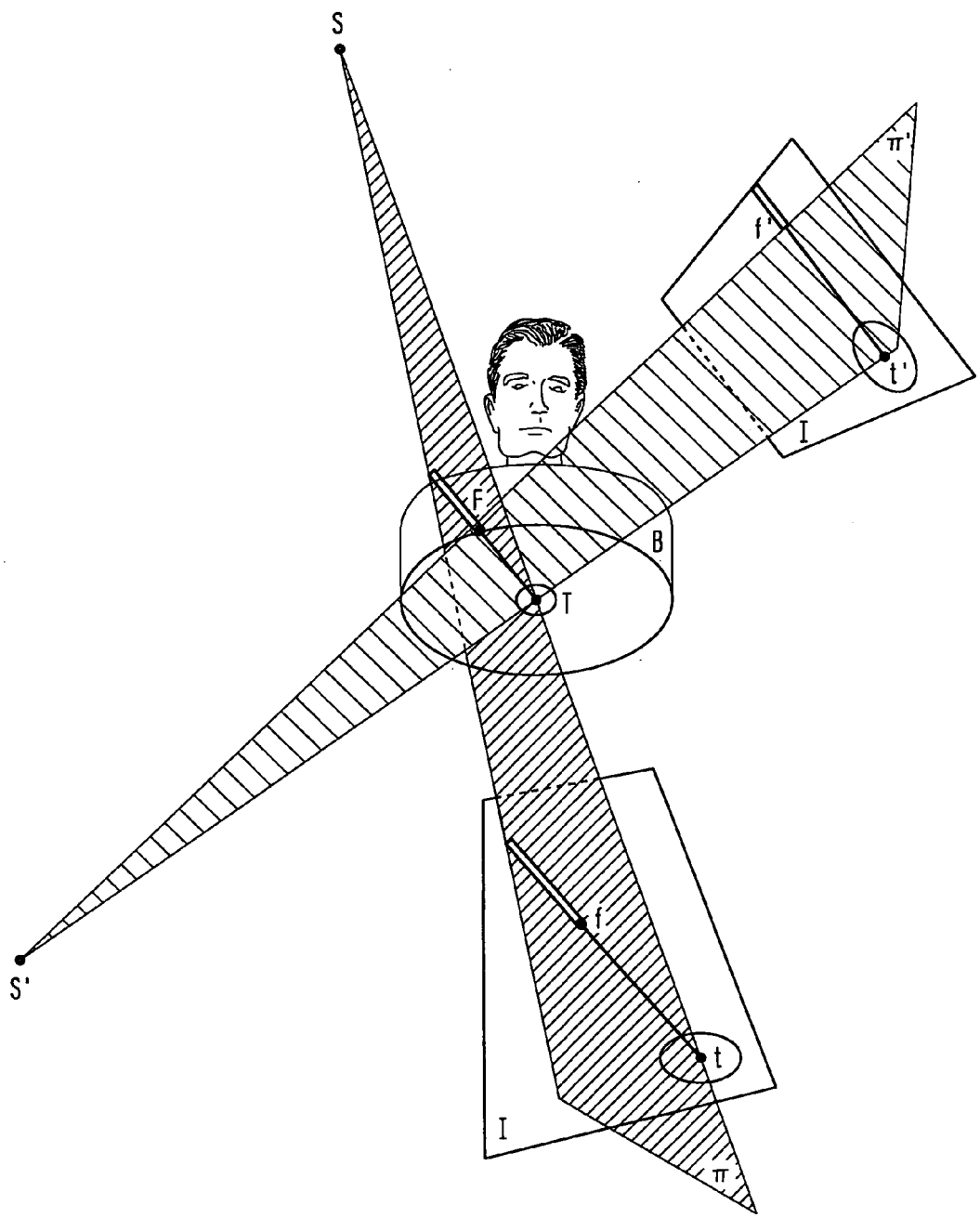
FIG. 3 shows a diagrammatic configuration of imaging radiation sources, image screens and a target area, helpful in understanding the invention.

FIG. 3 shows the geometry desirable for the surgeon. Preferably, the biopsy needle should be positioned such that its straight line continuation, or virtual extension, passes through a deep-seated target T inside the patient. During the manual procedure, the surgeon keeps the bottom end F of the needle on or near the patient's body and changes its direction until the virtual extension of the needle passes through the radiographic image t of the target T. The correct needle direction has to be verified on two radiographs that are taken from different angles.

In accordance with the present invention an apparatus has a geometrical configuration embodying a reasoned interpretation of what the surgeon seeks to do intuitively during a manual adjustment procedure. Clearly, the surgeon does not compute the exact or relative position and orientation of the C-arm and the image plane during a more or less refined "hit or miss" procedure. Rather, the surgeon proceeds by simple reasoning directly from radiographic images to the moving needle.

The subject matter of the above-mentioned copending patent applications entitled APPARATUS AND METHOD FOR POSITIONING A BIOPSY NEEDLE, APPARATUS AND METHOD FOR AUTOMATICALLY POSITIONING A BIOPSY NEEDLE, and APPARATUS AND METHOD FOR DETERMINING THE CORRECT INSERTION DEPTH FOR A BIOPSY NEEDLE is an adjunct to and is helpful to an understanding of the present invention and accordingly is herein included.

Referring again to FIG. 3, the imaging system is modelled approximately as a "pinhole camera" model. The optical center, S, represents the location of the X-ray source and the position and orientation of an image intensifier defines the image plane, I. The deep-seated target inside patient's body is indicated by T, with t being its radiographic image.

F is a fixed point from where the surgeon wishes to insert the biopsy needle. f is its radiographic image. The viewing plane $\pi$ is defined by the optical center, S, the target on the image, t, and the fixed point, F, and its radiographic image, f.

All the entities and reference letters relating to a second position of the X-ray and therefore to a second radiographic image are noted by prime, such as S', $\pi$', and so on.

Initially, it is recognized that the three-dimensional position of viewing plane $\pi$, while obtainable in accordance with the present disclosure as will be shown, is not known in a facile manner to the user.

Generally, images of all lines lying on the plane $\pi$ which do not pass through the optical center S, are collinear to the line ft on the radiographic image I. Since the depth of the target T, or $\|FT\|$, is unknown, the maximum information that can be obtained on the position and orientation of the biopsy needle from a sequence of images taken from a single viewpoint is the three dimensional position of the plane $\pi$. Accordingly, a first part of the algorithm in accordance with the present disclosure can be established, in Step I, as follows.

Any plane $\pi_1$ passing through the fixed point F, other than the plane $\pi$ itself, intersects the plane $\pi$ in one line. This line clearly contains the point F and therefore its image must pass through the image f of the fixed point F on the image on image plane I. The first two steps of the algorithm can now be defined, resulting in a method of accurately obtaining the three dimensional coordinates of the viewing plane $\pi$. A metallic, or other radiation-opaque, bar is rotated around the fixed point F in an arbitrary plane $\pi_1$ passing through the fixed point F. See FIG. 4, which illustrates the step of finding a three-dimensional line lying on the viewing plane $\pi$. The shortest distance of the projection line of the three-dimensional line from the target t on the image is called $h_1$.

This $h_1$ distance decreases as the angle between them closes, and projection line approaches line $L_1$, representing the intersection of the planes $\pi$ and $\pi_1$, and vanishes at the intersection of these two planes. This provides a simple way to control the metallic bar under automatic images guidance and move it until it lies on the plane $\pi$.

In a further step, Step II, a metallic (X-ray opaque) bar is rotated around the fixed point F in a second plane $\pi_2$ passing through the fixed point F, and different from $\pi_1$ used in the Step I, see FIG. 5, which illustrates the procedure for finding a second three-dimensional line on the viewing plane $\pi$. Preferably, the plane passing through F and orthogonal to $\pi_1$ is selected as $\pi_2$. The distance of its projection line from the target t on the image, is called $h_2$. This distance decreases as the projection line of $\pi_2$ approaches line $L_2$, representing the intersection of the planes $\pi$ and $\pi_2$ and this distance, $h_2$ vanishes at the intersection line of these two planes.

This provides a way to control a second metallic bar under automatic images guidance and move it until it also lies on the plane $\pi$. Now two distinct lines, $L_1$ and $L_2$, having a non-zero angle of intersection therebetween, are identified on the plane $\pi$. These lines uniquely define the plane $\pi$ in three dimensional space. This is the maximum information that can be had from a single viewpoint with no calibration data.

A next step, Step III, is the use of a second viewpoint. The radiographic image from a second viewpoint can be obtain either by moving the C-arm of the machine arbitrarily; the larger is the angle of rotation the more accurate is the resulting position and orientation of the needle.

The plane defined by the optical center, the X-ray source S' of the new configuration of the imaging system, the target T and the fixed point F is designated as $\pi$', analogous to plane $\pi$ in the previous determination. See FIG. 6 which shows the procedure for finding the right orientation for the biopsy needle.

A metallic bar is rotated around the fixed point F in the plane $\pi$ obtained in step II. The distance of its projection line, l', from the target t' on the image taken from the new viewpoint, is called h'. This distance decreases as one gets closer to the line L', representing the intersection of the planes $\pi$ and $\pi$' and this distance vanishes at the intersection of these two planes.

This provides a way to control the metallic bar manually or automatically using image guidance and move it until the line FT is found. FT is the line of intersection of the two flat planes $\pi$ and $\pi$' and it therefore represents a vector direction in space passing through the proposed fixed insertion point F and, when produced, through the target T. Now, the surgeon can be guided to the correct positioning of the biopsy needle. The next step in accordance with the invention, is to let the surgeon know how deep the target T is inside the patient. First a method disclosed in the copending application entitled APPARATUS AND METHOD FOR DETERMINING THE CORRECT INSERTION DEPTH FOR A BIOPSY NEEDLE will be described.

The cross ratio is a fundamental invariant of perspective projection. See, for example, O. D. Faugeras, Three-Dimensional Computer Vision: A Geometric Viewpoint; MIT Press, Cambridge, Mass.; 1993. This invariant can be used here to accurately compute FT, the depth of the target inside patient's body.

Referring to FIG. 7, consider the four points A, B, C, and D, on a line in space. The cross ratio of these four points can be defined as $$\frac{AB \times CD}{AC \times BD}.$$

The perspective projection of these four points on any plane and with respect to any projection center, for example {a, b, c, d} and {e, f, g, h} in FIG. 7 results in the same cross ratio between the projected points:

$$\frac{AB \times CD}{AC \times BD} = \frac{ab \times cd}{ac \times bd} = \frac{ef \times gh}{eg \times fh}$$

For the case of two markers, $M_1$ and $M_2$, on the metallic bar used in step III, such that $\|M_1F\|$ and $\|M_2F\|$ are accurately known, and $m_1'$ and $m_2'$, their radiographic images, are easily and accurately detectable, see FIG. 8. The assumptions made are reasonable and readily realized in practice. The cross ratio computed for the image points [m'1, m'2, f', t'] is the same as the cross ratio of the four points [$M_1$, $M_2$, F, T] in the three dimensional space. The positions of all these points other than T are known. FT is then computed from the following equation:

$$\|FT\| = \frac{\lambda \times \|M_1F\| \times \|M_2F\|}{\|M_1M_2\| - \lambda \times \|M_1F\|} \quad \text{where} \quad \lambda = \frac{\frac{\|f't'\|}{\|m'_2t'\|}}{\frac{\|m'_1f'\|}{\|m'_1m'_2\|}}$$

The positioning in accordance with the present disclosure is designed based on the algorithm disclosed above. FIGS. 12, 13, 14, and 16 show a design configuration. A part of the apparatus is a semi-circle that can rotate at least from 0 to 180 degrees around the center of a circular base. This rotation angle is designated by $\alpha$ in FIG. 12. This semi-circle has a second degree of freedom: it can also turn around its own baseline from 0 to 180 degrees. This rotation angle is designated by $\Theta$ in FIG. 12. A metallic bar can rotate on the plane defined by this semi-circle from 0 to 180 degrees. This rotation angle is noted by $\phi$ in FIG. 12. This provides all that is required. All rotations can be done either by hand, by command, or automatically. The parallel or serial connection between a computer, such as a personal computer (PC), and a positioning device can guide the system based on the minimization of $h_1$, $h_2$ and h' on the radiographic images. Further details about the interactive and automatic process are provided in appendix-A and appendix-B.

FIGS. 9, 10, and 11 provide bridging information to facilitate an understanding of the relationship between the foregoing algorithm and the design herein described. These figures include some of the constructions shown in previous figures and are helpful to bridging the steps between the geometric principles forming a basis for the present invention and the practical apparatus and method herein disclosed.

FIG. 9 shows the procedure utilized in finding one three dimensional line lying on the viewing plane $\pi$. This comprises positioning the semi-circle at an arbitrary position to define a plane $\pi_1$ and then moving the metallic bar mounted on the semi-circle to a position where its image passes through f and t on the image. This process can be done automatically. The metallic bar is moved to minimize the distance $h_1$ on the image. This process is not time-consuming and is readily carried out in real time.

FIG. 10 shows Step II, the process of finding a second three dimensional line lying on the viewing plane $\pi$. This is similar to the previous step, but the semi circle has turned by an angle in the order 90 degrees around its based line defining a new plane $\pi_2$.

FIG. 11 shows Steps III \& IV: Finding the right orientation of the biopsy needle and the depth of the target T inside the patient's body. This comprises positioning the semi-circle in the plane, $\pi'$ defined by the metallic bar in steps I and II, and then rotating the metallic bar until its radiographic view from the new viewpoint passes through f' and t'. The center of the circular base, F, and the target inside patient's body, T, lie on the both planes $\pi$ and $\pi'$. Their intersection is therefore FT the correct direction of the biopsy needle. The depth of the target, |FT|, can then be computed using the invariance of cross ratios by perspective projection; see the previous section on the geometrical description. The whole process, steps I through IV, can be done in real time and the surgeon can easily move the device and find the new orientation of the biopsy needle and depth of the target at any other contact point on the patient's body. This design lends itself readily to economical implementation.

The interactive system in accordance with the present invention has the advantage of being an independent unit which can be used together with any kind of X-ray fluoroscopes or C-arm imaging system and it needs no physical connections with the imaging system. The unit is entirely and readily portable. Furthermore, the operating surgeon has no radiation exposure at all during the search for the correct position.

FIG. 15 shows a protocol for the interactive system as herein described, in accordance with the invention. In this case the apparatus is fixed on the patient on top of the desired entry point defined by the surgeon. The surgeon works with the control device while looking at the radiographs and can be in the same room or in another room where the radiographic images can be observed without the surgeon's being exposed to the radiation.

These are the consecutive steps of the process.

A first plane is taken by fixing $\alpha=0$ and $\Theta=\Theta_1$. See FIG. 13. Note that $\Theta_1$ is quite arbitrary. A user can choose this plane so as to maintain a clear view of the metallic bar. This can be done using the control buttons, $\pi_1$, $+\alpha$, $-\alpha$, $+\Theta$ and $-\Theta$, as shown in FIG. 15.

The user then selects the proper angle $\phi$ by moving the metallic bar until its radiographic image passes through the target point. This can be done by using buttons $+\phi$ and $-\phi$ as in FIG. 15. The orientation of the metallic bar is then defined as:

$L_1=[\sin(\phi_1)\sin(\theta_1),\sin(\phi_1)\cos(\theta_1),\cos(\phi_1)]]$

See FIG. 13. Note that $\Theta_2$ is also arbitrary. A user can choose this plane in order to have a clear view of the metallic bar. This can be done using the control buttons, $\pi_2$, $+\Theta$, and $-\Theta$, as in FIG. 15.

A user finds the right angle $\phi$ by moving the metallic bar until its radiographic image passes through the target point. This can be done by using buttons $+\phi$ and $-\phi$, as in FIG. 15. The orientation of the metallic bar is then defined as:

$L_2=[\sin(\phi_2)\sin(\theta_2),\sin(\phi_2)\cos(\theta_2),\cos(\phi_2)]$

The final viewing plane (see FIG. 14) is then defined by $[\theta=\arc\sin(\|L_1 \wedge L_2\|)]$ and $$\alpha = \arccos\left(\frac{L_1[3]L_2[1] - L_1[1]L_2[3]}{\sqrt{(L_1[3]L_2[1] - L_1[1]L_2[3])^2 + (L_1[3]L_2[2] - L_1[2]L_2[3])^2}}\right)$$

where $\Lambda$ is the vector product defined in $R^3$, 3-dimensional space. The system will automatically move to the right position and the user has no need to adjust $\Theta$ and $\alpha$ in this case.

The user then uses the image on the second image intensifier or moves the C-arm to a new position.

The user finds the proper angle $\phi$ by moving the metallic bar until its radiographic images passes through the target point. This can be done by using buttons $+\phi$ and $-\phi$ as shown in FIG. 15. This is the correct orientation of the needle to be used for the biopsy.

In order to compute the depth of the target in accordance with the present invention, two other auxiliary needles are placed on the base line of the semi-circle; see FIG. 16. In order not to disturb the image of the main needle, these needles can be made in acrylic (transparent to X-ray) with only a few metallic markers to be aligned with the deep seated target. The determination of depth is arrived at by a process of triangulation in which a base-line forms the base of a triangle with the directions of the other two sides of the triangle being determined by respective angles subtended by the base and the respective side. Accordingly, the accuracy is greater where the angle between a needle and the metallic bar is greater. Hence, two alternative needles are provided so that that needle is utilized which is on the side of the obtuse angle made by the metallic bar with the plane of the diameter of the semicircle.

Each of these needles can rotate in the plane defined by this semi-circle around a fixed point other than the entry point. In accordance with the present embodiment, the two end points of the base line are used as the two centers of rotation. In the final position, the plane defined by the semi-circle also includes the deep seated target.

Once the correct orientation of the needle is found, the system activates that one of the auxiliary needles which has the greater angle with the main needle. The user moves this needle to align it with the target on the image. The system computes the depth of the target by computing the distance between the entry point and the intersection of the main needle and the active auxiliary needle. FIG. 16 shows this construction in detail.

The depth to the target, AC, is given by the trigonometric formula $$AC = \sin(\phi_1) \times \frac{AB}{\sin(\phi_1 - \phi)}$$

FIG. 17 shows a flowchart of the interactive process in accordance with the principles of the invention.

A semi-automatic system in accordance with the invention reduces the human interaction to the initial fixation of the unit on the patient, a definition, such as a manual definition, of the tumor on a computer display, and the final insertion of the needle, that will remain fully under the control of the surgeon.

The search for the optimal needle position and the calculation of the target depth is done automatically. The benefits of such a system are substantially increased speed of operation and thus less patient discomfort, reduced risk of patient motion, reduced radiation for the patient, and complete elimination of radiation for the surgeon during the search for the position.

The automatic system utilizes as a starting point the same basic arrangement as the manual version with additional features.

Three effectors are included, such as drive motors, to change the needle position. One each is utilized for $\Theta$, one for $\phi$, and one for the rotation $\alpha$, respectively. X-ray opaque markers are provided on the biopsy needle guidance so as to be visible on the fluoroscopic images and to be readily detectable by an image processing unit.

A computer is linked to the fluoroscope so as to be able to capture and store the X-ray images and to perform the necessary image processing to detect the needle markers. A computer stores and calculates needle positions and commands the effectors so as to move the needle positioner.

Furthermore, a user interface to the computer allows the surgeon to draw the outline of the target on the fluoroscopy image with a computer "mouse" coordinate translator or by using a graphics tablet.

Essentially, the procedure is as follows. The unit is installed on the patient. One single image from the fluoroscope is stored and displayed on the computer screen. The surgeon outlines manually the tumor on this image using the mouse. During this stage of the interaction, the fluoroscope is turn off, thereby reducing radiation exposure. The computer selects a first plane $\Theta$ and performs a task that is known as visual servoing. See FIG. 18. It changes the needle position, thereby varying $\phi$ and detects the needle markers on the fluoroscopic image. From the markers, it can determine the projection of the needle, that is the axial center-line of the needle produced or continued beyond the needle.

The closest distance of this "virtual needle" to the target in the image can be calculated. The position of the needle is changed until this distance is reduced to a minimal amount and the projection of the needle passes through the target. The parameters $\Theta$ and $\phi$ of the needle position are stored. This step is repeated for a different choice of $\Theta$ in order to find a second needle position. Then the C-arm position has to be changed, and the target must be outlined once again on a first image. From the two previous needle positions, the computer calculates the necessary rotations $\alpha$ and $\Theta$ to bring the needle in the final plane.

Then the visual servoing step is repeated. The final position $\phi$ is the one that passes through the target. The needle guidance system has to be blocked in that position, either using the effectors or by actuating an additional blocking or position locking device.

The fluoroscopy unit is switched on for two initial images that are used for outlining the target, and during the visual servoing steps. This procedure is usually very brief. The system then uses the needle markers in order to automatically compute the depth of the target from the entry point. Depending on the speed of the effectors, the described system is able to find the optimal needle position and the depth of the target in a few seconds. FIG. 19 shows a flowchart of this automatic process. FIG. 20 shows the connection and relationship between the different components of the automatic system.

It generally noted that apparatus parts should be X-ray transparent unless they are required to be visible in the image, such as, for example, needles and markers.

While the invention has been described in terms of exemplary embodiments, it will be apparent to one of skill in the art to which it pertains that various changes and modifications can be made without departing from the spirit of the invention. For example, circular scales are defined in the traditional manner of a circular protractor for portions of apparatus defining a plane and providing angle measure. Clearly, such parts need not be circular to provide such functions. Furthermore, it is noted that the cross-product, while conveniently defined and used in a particular manner herein, such as A,B and C,D, can utilize other dimensions in the constellation so as to obtain the depth. These are equivalent cross-product functions and can be substitute where appropriate. Such changes and modifications and the like are intended to be within the scope of the invention which is defined by the claims following.

What is claimed is:

1. Apparatus for determining the required insertion depth for a biopsy needle priorly aligned for proper insertion into the body of a patient at a selected point on a surface of said body, so as to enter in a straight line passing through a designated target region within said body by the use of first and second image planes, such that at said proper depth, an end of said needle just reaches said target area, said apparatus comprising:
- a base portion including a circle portion having a center point;
- a planar semicircular portion mounted onto said base portion such that the diameter of said semicircular portion is concentric with said center point and rotatable thereabout, said semicircle portion being further rotatable about a straight line through said diameter;
- a straight pointing device having one end thereof pivotably affixed to said center point and being constrained for movement within a plane defined by said planar semicircular portion; and
- at least one straight pointing needle having one end thereof pivotably affixed at one end of said diameter of said semicircular portion and being constrained for movement within a plane defined by said planar semicircular portion;
- means for measuring an angle θ of said plane defined by said semicircular portion relative to said base portion, an angle φ of said pointing device relative to said base portion, and an angle $\phi_1$ defined by said at least one pointing needle relative to said base portion; and
- a further pointing needle having one end thereof pivotably affixed at the other end of said diameter of said semicircular portion and being constrained for movement within said plane defined by said planar semicircular portion.

2. Apparatus for determining the required insertion depth for a biopsy needle in accordance with claim 1, wherein at least one of said pointing needles is made of a substantially radiation-transparent material.

3. Apparatus for determining the required insertion depth for a biopsy needle in accordance with claim 1, wherein at least one of said pointing needles is made of a substantially radiation-transparent material and includes imbedded therein markers that are relatively radiation-opaque as compared with said radiation-transparent material.

4. Apparatus for positioning or aligning a biopsy needle for proper insertion in accordance with claim 3 wherein said first and second planar measuring portions include a read-out device for reading out angles between said base, said first and said second planar measuring portions, and said pointing device.

5. Apparatus for positioning or aligning a biopsy needle for proper insertion in accordance with claim 4 wherein said read-out device is an electronic digital device.

6. Apparatus for positioning or aligning a biopsy needle for proper insertion in accordance with claim 4 including a locking device for holding said angles.

7. Apparatus for determining the required insertion depth for a biopsy needle in accordance with claim 1, including computing apparatus for determining said depth by solving the equation $$AC = \sin(\phi_1) \times \frac{AB}{\sin(\phi_1 - \phi)}.$$

8. Apparatus for determining the required insertion depth for a biopsy needle priorly aligned for proper insertion into the body of a patient at a selected point on a surface of said body, so as to enter in a straight line passing through a designated target region within said body by the use of first and second image planes, such that at said proper depth, an end of said needle just reaches said target area, said apparatus comprising:
- a base including a first planar measuring portion having a center point;
- a second planar measuring portion mounted onto said base portion such that a center point of said second measuring portion is concentric with said center point of said first planar measuring portion so that said second planar measuring portion is rotatable about said center point, said second planar measuring portion being further rotatable about a straight line through its center; and
- an essentially straight pointing device having one end thereof pivotably affixed to said center point and being constrained for movement within a plane defined by said planar semicircular portion; and
- at least one essentially straight pointing needle having one end thereof pivotably affixed at one end of said straight line of said semicircular portion and being constrained for movement within a plane defined by said planar semicircular portion;
- means for measuring an angle Θ of said plane defined by said second planar measuring portion relative to said base portion, an angle φ of said pointing device relative to said base portion, and an angle $\phi_1$ defined by said at least one pointing needle relative to said base portion; and
- a further pointing needle having one end thereof pivotably affixed at the other end of said straight line and being constrained for movement within said plane defined by said second planar measuring portion.

9. Apparatus for determining the required insertion depth for a biopsy needle in accordance with claim 8, wherein at least one of said pointing needles is made of relatively radiation-transparent material.

10. Apparatus for determining the required insertion depth for a biopsy needle in accordance with claim 8, wherein at least one of said pointing needles is made of relatively radiation-transparent material and includes imbedded therein radiation-opaque markers.

11. Apparatus for determining the required insertion depth for a biopsy needle in accordance with claim 8, wherein said depth is obtained by solving the equation $$AC = \sin(\phi_1) \times \frac{AB}{\sin(\phi_1 - \phi)}.$$

12. Apparatus for determining the required insertion depth of a biopsy needle to be inserted at a selected point on the body of a patient so that a sampling end of said needle just reaches to a designated target area within said body, said apparatus comprising:
- at least one straight calibrated pointing device, having a pivot point at one end thereof, and aligned to point through said selected point in a straight line passing through said designated target region, an image of said pointing device being formed on each of first and second image planes by utilizing radiation from respective first and second radiation source positions, along with images corresponding to said selected point and said target area; and
- needle means for casting an image on one at least one of said image planes, said needle means being pivotably mounted at a further pivot point different from said pivot point of said pointing device and being constrained for movement in plane defined by said pivot point, said further pivot point and by said pointing device.

13. Apparatus for determining a proper insertion depth of a biopsy needle to be inserted at a selected point on the body of a patient so that a sampling end of said needle just reaches to a designated target area within said body, said apparatus comprising:

at least one straight calibrated pointing device pivoted at one end thereof at a pivot point;

positioning means for automatically positioning or aligning said at least one straight calibrated pointing device as a guide for a biopsy needle for proper insertion into the body of a patient from a selected point on a surface of said body, so as to enter in a straight line passing through a designated target region within said body, in conjunction with an imaging system utilizing radiation from a first source position for deriving a first radiographic image on a first image plane of a portion of said body including a first image of said selected point and a first image of said target region, said first source position, said first image of said selected point, and said first image of said target region defining a first viewing plane π, said imaging system utilizing radiation from a second source position for deriving a second radiographic image on a second image plane of said portion of said body, including a second image of said selected point and a second image of said target region, said second source position, said second image of said selected point, and said second image of said target region defining a second viewing plane π', said positioning means comprising:

measurement means for determining an angle $\Theta_1$ for a selected first auxiliary plane and an angle $\Theta_2$ for a selected second auxiliary plane with respect to a selected set of coordinates and for storing said angles, said second plane angle being different from said first plane angle such that said first and second auxiliary planes form an intersection line;

means for constraining said calibrated pointing device for moving rotatably about said selected point and within said first auxiliary plane to a first angle of inclination $\phi_1$ relative to a set of coordinates and for controlling said calibrated pointing device such that a projection or extension of an image of said calibrated pointing device on said first image plane passes through said first image of said target region and for storing said angle $\phi_1$, said alignment and control means further controlling said calibrated pointing device for moving rotatably about said selected point and within said second auxiliary plane to a second angle of inclination $\phi_2$ relative to said set of coordinates such that a projection or extension of an image of said calibrated pointing device on said second image plane passes through said second image of said target region and for storing said angle $\phi_2$, whereby said first viewing plane π is uniquely defined by said angles $\Theta_1$, $\Theta_2$, $\phi_1$, and $\phi_2$ relative to said set of coordinates;

means for determining orientation angles α and $\Theta_3$ of said viewing plane π from stored values of said angles $\Theta_1$, $\Theta_2$, $\phi_1$, and $\phi_2$, and storing said angles α and $\theta_3$; and means for moving said calibrated pointing device rotatably about said selected point and within said first viewing plane π, as defined by said angles α and $\Theta_3$, to a third angle of inclination $\phi_3$ relative to said set of coordinates such that a projection or extension of an image of said calibrated pointing device on said second image plane passes through said further image of said target region, whereby said pointer points directly through said selected point toward said target region, such that that respective images of pointing device are formed on said first and second image planes, along with images corresponding to said selected point and said target area; and needle means for casting an image on one at least one of said image planes, said needle means being pivotably mounted at a further pivot point different from said pivot point of said pointing device and being constrained for movement n plane defined by said pivot point, said further pivot point and by said pointing device.

14. A method for determining the required insertion depth for a biopsy needle so as to just reach a selected target area within a body, wherein a proper direction for insertion of said biopsy needle has been priorly determined from a radiographic image on a viewing plane such that an extension of said direction of said biopsy needle from a selected insertion point into said body in a straight line leads through a selected target area, comprising the steps of:

placing a biopsy needle such that an extension of said biopsy needle leads to a selected target area defining a plane containing said biopsy needle;

placing a pointing needle such that an extension of said pointing needle can lead through said selected target area;

placing a pointing needle, pivoted at one end and constrained to move within said plane;

adjusting said pointing needle, until a prolongation of the line of an image of said pointing needle on said plane intersects said selected target area; and calculating said required insertion depth from knowledge of a base line length AC joining said pivot point and said selected insertion point and respective angles, $\phi$ and $\phi_1$, of said biopsy needle and said pointing needle.

15. A method for determining the required insertion depth for a biopsy needle in accordance with claim 14 including computing apparatus for determining said required insertion depth by solving the equation $$AC = \sin(\phi_1) \times \frac{AB}{\sin(\phi_1 - \phi)}.$$

16. Apparatus for determining the required insertion depth for a biopsy needle priorly aligned for proper insertion into the body of a patient at a selected point on a surface of said body, so as to enter in a straight line passing through a designated target region within said body by the use of first and second image planes, such that at said proper depth, an end of said needle just reaches said target area, said apparatus comprising:

a base portion including a circle portion having a center point;

a planar semicircular portion mounted onto said base portion such that the diameter of said semicircular portion is concentric with said center point and rotatable thereabout, said semicircle portion being further rotatable about a straight line through said diameter;

a straight pointing device having one end thereof pivotably affixed to said center point and being constrained for movement within a plane defined by said planar semicircular portion; and first and second substantially straight pointing needles, each having one end thereof pivotably affixed at a respective end of said diameter of said semicircular portion and being constrained for movement within a plane defined by said planar semicircular portion.

17. Apparatus for determining the required insertion depth for a biopsy needle in accordance with claim 16, including means for measuring an angle θ of said plane defined by said semicircular portion relative to said base portion, an angle φ of said pointing device relative to said base portion, and a respective angle $\phi_1$, $\phi_2$ defined by each of said pointing needles relative to said base portion.

18. Apparatus for determining the required insertion depth for a biopsy needle in accordance with claim 17, wherein at least one of said pointing needles is made of a substantially radiation-transparent material.

19. Apparatus for determining the required insertion depth for a biopsy needle in accordance with claim 18, wherein said pointing needles are made of a substantially radiation-transparent material and include imbedded therein markers that are relatively radiation-opaque as compared with said radiation-transparent material.

20. Apparatus for determining the required insertion depth for a biopsy needle in accordance with claim 19, including computing apparatus for determining said depth by solving the equation $$AC = \sin(\phi_1) \times \frac{AB}{\sin(\phi_1 - \phi)}.$$

21. Apparatus for positioning or aligning a biopsy needle for proper insertion into the body of a patient from a selected point on a surface of said body, so as to enter in a straight line passing through a designated target region within said body, in conjunction with an imaging system utilizing radiation from a first source position for deriving a first radiographic image on a first image plane of a portion of said body including a first image of said selected point and a first image of said target region, said first source position, said first image of said selected point, and said first image of said target region defining a first viewing plane π, said imaging system utilizing radiation from a second source position for deriving a second radiographic image on a second image plane of said portion of said body, including a second image of said selected point and a second image of said target region, said second source position, said second image of said selected point, and said second image of said target region define a second viewing plane π', said apparatus comprising:
first measuring circle means for establishing a first auxiliary plane at a first plane angle $\theta_1$ with respect to a selected set of coordinates and for constraining a pointer for moving rotatably about said selected point and within said first auxiliary plane to a first angle of inclination $\theta_1$ relative to said set of coordinates such that a projection or extension of an image of said pointer on said first image plane passes through said first image of said target region;
second measuring circle means for establishing a second auxiliary plane at a second plane angle $\theta_2$ with respect to said selected set of coordinates, said second plane angle being different from said first plane angle such that said first and second auxiliary planes form an intersection line and for constraining a pointer for moving rotatably about said selected point and within said second auxiliary plane to a second angle of inclination $\theta_2$ relative to said set of coordinates such that a projection or extension of an image of said pointer on said first image plane passes through said first image of said target region, whereby said first viewing plane π is uniquely defined by said angles $\theta_1$, $\theta_2$, $\phi_1$, and $\phi_2$ relative to said set of coordinates;
means for setting said pointer for moving rotatably about said selected point and within said first viewing plane π, now uniquely defined, to a third angle of inclination $\phi_3$ relative to said set of coordinates such that a projection or extension of an image of said pointer on said second image plane passes through said further image of said target region, whereby said pointer points directly through said selected point toward said target region.

22. A method for positioning or aligning a biopsy needle for proper insertion into the body of a patient from a selected point on a surface of said body, so as to enter in a straight line passing through a designated target region within said body, said method comprising the steps of:
utilizing radiation from a first source position for deriving a first radiographic image on a first image plane of a portion of said body including a first image of said selected point and a first image of said target region, said first source position, said first image of said selected point, and said first image of said target region defining a first viewing plane π;
establishing a first auxiliary plane at a first plane angle $\theta_1$ with respect to a selected set of coordinates;
moving a pointer rotatably about said selected point and within said first auxiliary plane to a first angle of inclination $\phi_1$ relative to said set of coordinates such that a projection or extension of an image of said pointer on said first image plane passes through said first image of said target region;
establishing a second auxiliary plane at a second plane angle $\theta_2$ with respect to said selected set of coordinates, said second plane angle being different from said first plane angle such that said first and second auxiliary planes form an intersection line;
moving said pointer rotatably about said selected point and within said second auxiliary plane to a second angle of inclination $\phi_2$ relative to said set of coordinates such that a projection or extension of an image of said pointer on said first image plane passes through said first image of said target region, whereby said first viewing plane it is uniquely defined by said angles $\theta_1$, $\theta_2$, $\phi_1$, and $\phi_2$ relative to said set of coordinates;
utilizing radiation from a second source position for deriving a second radiographic image on a second image plane of said portion of said body, including a second image of said selected point and a second image of said target region, said second source position, said second image of said selected point, and said second image of said target region define a second viewing plane π';
moving said pointer rotatably about said selected point and within said first viewing plane π, now uniquely defined, to a third angle of inclination $\phi_3$ relative to said set of coordinates such that a projection or extension of an image of said pointer on said second image plane passes through said further image of said target region, whereby said pointer points directly through said selected point toward said target region.

23. A method for positioning a guide for a biopsy needle for its proper insertion into said body of a patient from a selected point on a surface of said body, so as to enter in a straight line passing through a designated target region within said body, in conjunction with an imaging system utilizing radiation from first and second source positions for deriving first and second radiographic images, said method including:
- (a) selecting a first auxiliary plane at an angle $\theta_1$; moving said guide within said first auxiliary plane to an angle $\phi_1$ so as to cause said guide image on said first image plane to be aligned in a straight line through said target region;
- (b) storing said angle $\phi_1$;
- (c) selecting a second, different, auxiliary plane at an angle $\theta_1$;
- (d) moving said guide to an angle $\phi_2$ within said second auxiliary plane so as to cause said guide image on said second image plane to be aligned in a straight line through said target region;
- (e) storing values for said angles $\theta_2$ and $\phi_2$;
- (f) calculating, by utilizing values stored for said angles, rotations $\alpha$ and $\theta$ so as to derive a first viewing plane $\pi$; and
- (g) moving said guide within said first viewing plane $\pi$ to an angle $\phi_3$ so as to cause said guide image on said second image plane to be aligned in a straight line through said target region, whereby said guide is properly aligned.

24. A method for positioning a guide for a biopsy needle in accordance with claim 23, wherein $\alpha$ and $\theta$ are defined by $$[\theta = \arcsin(\|L_1 \text{wedge} L_2\|)] \text{ and}$$

$$\alpha = \arccos\left(\frac{L_1[3]L_2[1] - L_1[1]L_2[3]}{\sqrt{(L_1[3]L_2[1] - L_1[1]L_2[3])^2 + (L_1[3]L_2[2] - L_1[2]L_2[3])^2}}\right)$$

where $\Lambda$ is the vector product defined in $^3 2$, 3-dimensional space.

25. Apparatus for positioning or aligning a biopsy needle for proper insertion into the body of a patient from a selected point on a surface of said body, so as to enter in a straight line passing through a designated target region within said body, in conjunction with an imaging system utilizing radiation from a first source position for deriving a first radiographic image on a first image plane of a portion of said body including a first image of said selected point and a first image of said target region, said first source position, said first image of said selected point, and said first image of said target region defining a first viewing plane $\pi$, said imaging system utilizing radiation from a second source position for deriving a second radiographic image on a second image plane of said portion of said body, including a second image of said selected point and a second image of said target region, said second source position, said second image of said selected point, and said second image of said target region define a second viewing plane $\pi'$, said apparatus comprising:
- measuring circle means having a first position for establishing a first auxiliary plane at a first plane angle $\theta_1$ with respect to a selected set of coordinates and for constraining a pointer for moving rotatably about said selected point and within said first auxiliary plane to a first angle of inclination $\phi_1$ relative to said set of coordinates such that a projection or extension of said image of said pointer on said first image plane passes through said first image of said target region;
- said measuring circle means having a second position for establishing a second auxiliary plane at a second plane angle $\theta_2$ with respect to said selected set of coordinates, said second plane angle being different from said first plane angle such that said first and second auxiliary planes form an intersection line and for constraining a pointer for moving rotatably about said selected pint and within said second auxiliary plane to a second angle of inclination $\phi_2$ relative to said set of coordinates such that a projection or extension of an image of said pointer on said first image plane passes through said first image of said target region, whereby said first viewing plane it is uniquely defined by said angles $\theta_1$, $\theta_2$, $\phi_1$, and $\phi_2$ relative to said set of coordinates;
- means for setting said pointer for moving rotatably about said selected point and within said first viewing plane $\pi$, now uniquely defined, to a third angle of inclination $\phi_3$ relative to said set of coordinates such that a projection or extension of an image of said pointer on said second image plane passes through said further image of said target region, whereby said pointer points directly through said selected point toward said target region.

* * * * *